United States Patent
Dove

(10) Patent No.: US 11,872,038 B2
(45) Date of Patent: Jan. 16, 2024

(54) MEDICAL DEVICE INCLUDING DIFFUSE REFLECTOR FOR DETECTING FLUID PARAMETERS

(71) Applicant: Covidien LP, Mansfield, MA (US)

(72) Inventor: Jacob D. Dove, Lafayette, CO (US)

(73) Assignee: COVIDIEN LP, Mansfield, MA (US)

( * ) Notice: Subject to any disclaimer, the term of this patent is extended or adjusted under 35 U.S.C. 154(b) by 217 days.

(21) Appl. No.: 17/168,935

(22) Filed: Feb. 5, 2021

(65) Prior Publication Data
US 2022/0071516 A1     Mar. 10, 2022

Related U.S. Application Data

(60) Provisional application No. 63/075,001, filed on Sep. 4, 2020.

(51) Int. Cl.
| | | |
|---|---|---|
| A61B 5/1455 | (2006.01) |
| A61B 5/1459 | (2006.01) |
| A61B 5/145 | (2006.01) |
| G01N 21/64 | (2006.01) |
| A61M 25/00 | (2006.01) |
| G01N 21/47 | (2006.01) |
| A61B 5/00 | (2006.01) |

(52) U.S. Cl.
CPC ........ *A61B 5/1459* (2013.01); *A61B 5/14503* (2013.01); *A61B 5/14556* (2013.01); *A61B 5/6852* (2013.01); *A61M 25/0017* (2013.01); *A61M 25/0021* (2013.01); *G01N 21/47* (2013.01); *G01N 21/6486* (2013.01)

(58) Field of Classification Search
CPC . A61B 5/1459; A61B 5/14503; A61B 5/1455; A61B 5/14556
See application file for complete search history.

(56) References Cited

U.S. PATENT DOCUMENTS

| | | |
|---|---|---|
| 6,379,969 B1 | 4/2002 | Mauze et al. |
| 7,181,096 B2 | 2/2007 | Matsumoto et al. |
| 8,553,649 B2 | 10/2013 | Zhang et al. |
| 8,649,836 B2 | 2/2014 | Shimizu et al. |
| 8,715,254 B2 | 5/2014 | Nishtala |

(Continued)

FOREIGN PATENT DOCUMENTS

| | | |
|---|---|---|
| WO | 2019/143676 A1 | 7/2019 |
| WO | 2020/006549 A1 | 1/2020 |

OTHER PUBLICATIONS

Wolfbeis, "Luminescent sensing and imaging of oxygen: Fierce competition to the Clark electrode," Methods, Models & Techniques, Prospects & Overviews, Bioessays 37: Jun. 2015, pp. 921-928.

(Continued)

*Primary Examiner* — Marjan Fardanesh
(74) *Attorney, Agent, or Firm* — Fletcher Yoder, P.C.

(57) ABSTRACT

An example system includes an elongated body, a fluorescent material, and a diffuse reflector. The elongated body defines a lumen and includes a proximal portion and a distal portion. The fluorescent material is configured to be in fluid communication with a fluid in the lumen. The diffuse reflector is configured to diffuse excitation light received from an excitation light source and direct the diffused excitation light toward the fluorescent material and diffuse the fluoresced light received from the fluorescence material and direct the fluoresced light toward a fluorescent light detector.

9 Claims, 10 Drawing Sheets

(56) References Cited

U.S. PATENT DOCUMENTS

| | | |
|---|---|---|
| 8,848,188 B2 | 9/2014 | Nishino et al. |
| 9,848,787 B2 | 12/2017 | White et al. |
| 10,398,365 B2 | 9/2019 | Takahashi et al. |
| 2007/0263210 A1 | 11/2007 | Taguchi et al. |
| 2018/0199829 A1 | 7/2018 | White et al. |
| 2019/0069831 A1 | 3/2019 | Kuck et al. |
| 2019/0086316 A1 | 3/2019 | Rice et al. |
| 2019/0150801 A1 | 5/2019 | Suehara et al. |
| 2020/0022636 A1 | 1/2020 | Suehara et al. |
| 2020/0022638 A1 | 1/2020 | Suehara et al. |
| 2020/0064172 A1 | 2/2020 | Tabaczewski et al. |
| 2020/0158548 A1 | 5/2020 | Rice et al. |

OTHER PUBLICATIONS

U.S. Appl. No. 16/854,592, filed Apr. 21, 2020 naming inventor David J. Miller.

Labsphere, "Technical Guide: Integrating Sphere Uniform Light Source Applications," May 2008, 16 pp.

U.S. Appl. No. 17/013,294, filed Sep. 4, 2020 naming inventor Jacob D. Dove.

Mahoney, "Point-of-Care Urinalysis with Emerging Sensing and Imaging Technologies", Journal of The Electrochemical Society, vol. 167, Dec. 11, 2019, 15 pp.

Nawrot, "A Fluorescent Biosensors for detection Vital Body Fluids' Agents", Sensors, Jul. 24, 2018, 28 pp.

US 11,872,038 B2

MEDICAL DEVICE INCLUDING DIFFUSE REFLECTOR FOR DETECTING FLUID PARAMETERS

This application claims the benefit of U.S. Provisional application No. 63/075,001, entitled "MEDICAL DEVICE INCLUDING DIFFUSE REFLECTOR FOR DETECTING FLUID PARAMETERS" and filed on Sep. 4, 2020, which is incorporated herein by reference in its entirety.

TECHNICAL FIELD

This disclosure relates to medical devices, more particularly, to catheters.

BACKGROUND

Medical devices, such as catheters, may be used to assist a patient in voiding their bladder. In some instances, such catheters may be used during and/or after surgery. In the case of using a catheter to assist a patient in voiding their bladder, a Foley catheter is a type of catheter used for longer time periods than a non-Foley catheter. Some Foley catheters are constructed of silicon rubber and include an anchoring member, which may be an inflatable balloon inflated in a patient's bladder to serve as an anchor, so a proximal end of the catheter does not slip out of the patient's bladder.

SUMMARY

The disclosure describes catheters (e.g., a Foley catheter) and systems that sense one or more parameters of a fluid, such as oxygenation, flowing through the catheter by stimulating and measuring fluorescence of a fluorescent material in fluid communication with the fluid, and methods of making and using the catheters and systems. In some examples, catheters and systems may include a diffuse reflector and/or an integrating sphere to reduce noise from ambient light and reduce variation due to changes in alignment between the excitation light source, the fluorescent material, and the fluorescent light detector.

In one example, this disclosure describes a system that includes an elongated body, a fluorescent material, and a diffuse reflector. The elongated body defines a lumen and includes a proximal portion and a distal portion. The fluorescent material is configured to be in fluid communication with a fluid in the lumen. The diffuse reflector is configured to diffuse excitation light received from an excitation light source and direct the diffused excitation light toward the fluorescent material, and diffuse the fluoresced light received from the fluorescence material and direct the fluoresced light toward a fluorescent light detector.

In another example, this disclosure describes a method that includes controlling an excitation light source to emit excitation light toward a first diffuse reflector. The first diffuse reflector is configured to diffuse the emitted excitation light to expose a fluorescent material to the emitted excitation light. The fluorescent material is disposed within a lumen defined by an elongated body comprising a proximal portion and a distal portion. The fluorescent material is configured to fluoresce light toward a second diffuse reflector when exposed to the emitted excitation light. The method further includes detecting, with a fluorescent light detector, an amount of fluoresced light from the second diffuse reflector. The second diffuse reflector is configured to diffuse the fluoresced light to expose the fluorescent light detector to the fluoresced light. The method further includes determining, based on the amount of the detected fluoresced light, at least one of an amount of oxygen or a concentration of oxygen in the fluid within the lumen.

In another example, this disclosure describes a system that includes an elongated body defining a lumen and an integrating sphere disposed within the lumen. The elongated body includes a proximal portion and a distal portion. The integrating sphere includes a housing, a fluorescent material, and a diffuse reflector. The housing includes at least one aperture and is configured to allow the liquid to enter and exit the housing. The fluorescent material is disposed on at least a portion of an inner surface of the housing. The fluorescent material is configured to be in fluid communication with a fluid within the lumen. The diffuse reflector forms at least a portion of an inner surface of the housing. The diffuse reflector is configured to diffuse excitation light received from an excitation light source within the lumen, direct the diffused excitation light towards the fluorescent material, and diffuse the fluoresced light received from the fluorescent material within the integrating sphere.

The details of one or more examples are set forth in the accompanying drawings and the description below. Other features, objects, and advantages will be apparent from the description and drawings, and from the claims.

DETAILED DESCRIPTION

Figure 1:
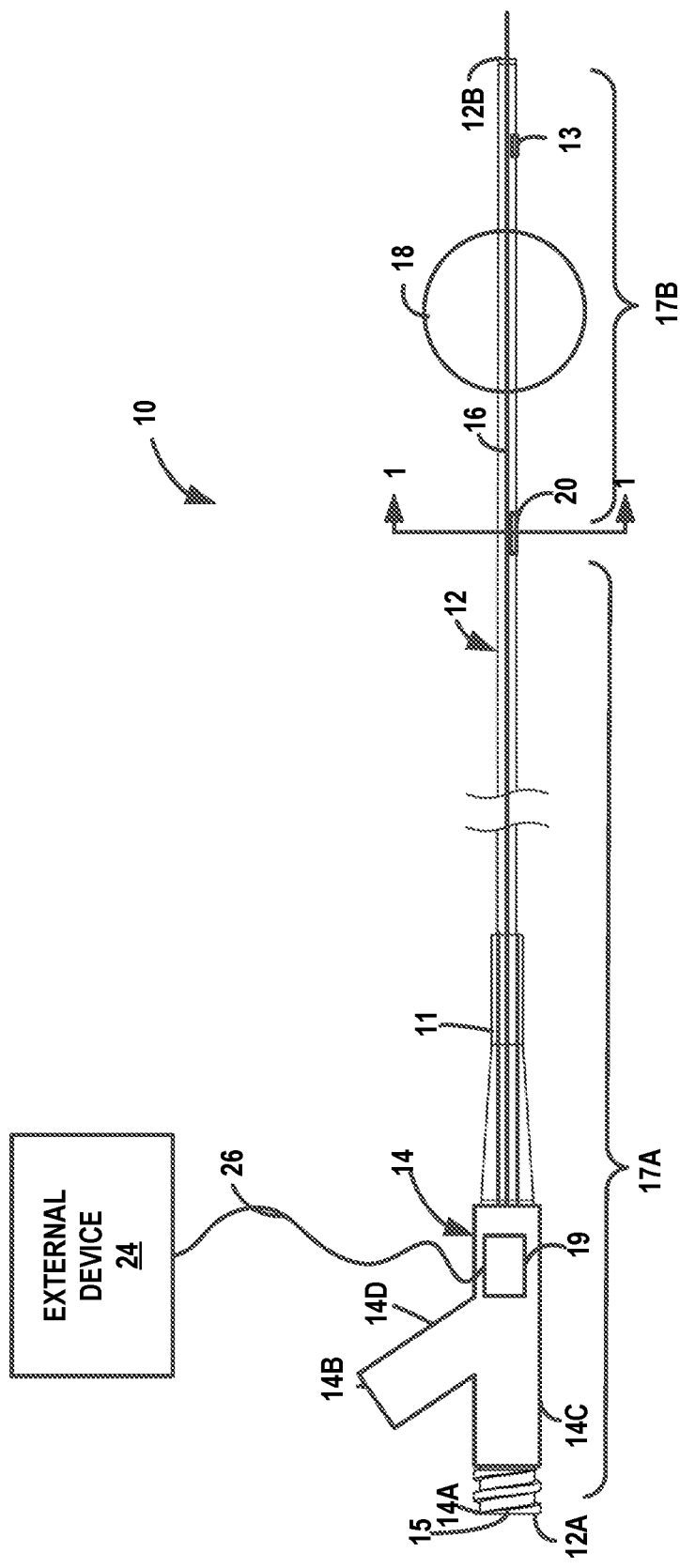
FIG. 1 is a diagram illustrating an example medical device according to the techniques of this disclosure.

In general, the disclosure describes example medical devices, systems, and techniques for determining oxygenation (e.g., an amount of oxygen or an oxygen concentration) and/or other parameters of a fluid. As will be described below, examples of the disclosure may include catheters (e.g. a Foley catheter or other urinary or non-urinary catheter) and/or catheter attachments (e.g., configured to be attached to a catheter) configured with a fluorescent material in a fluid (e.g., urine) within a lumen of the catheter (e.g., the drainage lumen or lumen in fluid communication with the drainage lumen) and a diffuse reflector in the optical path between an excitation light source and the fluorescent material and/or between a fluorescent light detector and the fluorescent material. One or more sensors positioned within or proximate to the catheter are configured to stimulate and sense a fluorescence response from the fluorescent material in the fluid. The sensed fluorescence response of the fluorescent material may correspond to one or more parameters of the fluid, such as oxygenation or flow rate. In some examples, all or a portion of the one or more sensors may be removably coupled to the catheter body and/or catheter attachment body, e.g., such that the catheter body and/or catheter attachment may be disposed after use but all or a portion of the sensor may be reused with another catheter body and/or catheter attachment.

In some examples, the sensed parameters may be used to monitor urine output/rate of urine production of a patient and/or the amount of oxygen dissolved in the urine. Such information may be useful in monitoring the renal function of the patient, e.g., while the catheter is inserted within the patient, to detect conditions that may damage or inhibit renal function. As one example, acute kidney injury (AKI) is a complication that may occur after major surgeries, such as cardiac surgery, and other operations that are long and involve significant blood loss or fluid shifts. A primary cause of surgery-associated AKI may be hypoxia of the kidneys. When the body becomes stressed, such as during cardiac surgery, blood flow may be reduced to vital organs in a relatively consistent sequence based on the criticality of the organs. For example, the skin may be the first to realize reduced blood flow, followed by the intestines and then the kidneys, then the brain and then the heart. The skin and the intestines may withstand short hypoxic episodes and recover normal function, but the kidneys can be damaged with even brief hypoxic episodes.

This resulting renal hypoxia may cause degradation of renal function, which, after one to three days, e.g., may cause a reduced urine output and/or an accumulation of waste products in the bloodstream. This accumulation of fluid and waste products may delay the recovery of the patient leading to more extended and expensive hospital stays and sometimes requiring renal replacement therapy. Systemic vital signs like cardiac output, blood pressure, and hematocrit may be useful for detecting the accumulation of these waste products but may not always be sufficient to properly monitor the kidneys. One approach for detecting symptoms of AKI relatively early is to monitor the oxygenation status of a patient's kidneys. However, accurate monitoring may be challenging due to the inaccessibility of the kidneys, which are deep in the abdominal cavity and relatively difficult to probe using spectroscopy techniques. For example, near-Infrared spectroscopy (NIRS) may measure regional oximetry and may have some utility in infants and slender adults but may not operate with the depth of penetration and specificity required for most adults.

The present disclosure describes example medical devices configured to monitor, or aid in monitoring of, kidney function of patients, such as patients at risk of developing AKI. Medical devices described herein may include a catheter and/or a catheter attachment configured with a fluorescent material within a lumen of the catheter in fluid communication with urine and one or more sensors including a diffuse reflector configured to stimulate and sense a fluorescence response from the fluorescent material that corresponds to parameters of the urine that are indicative of kidney function, such as oxygenation of the kidneys. In some examples, medical devices described herein may be configured to monitor the amount of oxygen dissolved in the urine coming from the bladder, as such a measurement may more accurately reflect the oxygenation of the kidneys. For example, dissolved oxygen in a patient's urine and bladder may correlate to perfusion and/or oxygenation of the kidneys, which is indicative of renal function, and may be detected relatively early and accurately compared to more variable or less responsive indicators of renal function, such as urine output or waste product accumulation. The decay of fluorescence response of the fluorescent material may indicate the amount of oxygen dissolved in the urine.

In some instances, medical devices described herein may include a diffuse reflector in the optical path between an excitation light source and the fluorescent material and/or between a fluorescent light detector and the fluorescent material. For example, detection and/or measurement of a fluorescence response of the fluorescent material be sensitive to interactions of the excitation and/or fluorescent light with background materials, ambient light from the environment, the illumination angle of the excitation light source with respect to the fluorescent material, the view angle of the fluorescent light detector, and the like. Variations in detection and/or measurement of the fluorescent response of the fluorescent material due to the factors above cause uncertainty in a determination of the amount of fluorescence response due to oxygenation of the urine as opposed to the other factors. By using a diffuse reflector in the optical path between an excitation light source and the fluorescent material and/or between a fluorescent light detector and the fluorescent material, medical devices described herein may reduce and/or eliminate variation in the detection and/or measurement of the fluorescent response of the fluorescent material due to variations in the illumination angle of the excitation light source and the view angle of the fluorescent light detector. By using a diffuse reflector and fluorescent material within a housing, such as an integrating sphere, medical devices described herein may further reduce and/or eliminate variation in the detection and/or measurement of the fluorescent response of the fluorescent material due to interactions of the excitation and/or fluorescent light with background materials and ambient light form the environment.

For ease of description, examples of the disclosure are primarily described with regard to a catheter, such as a Foley catheter, being employed as a urinary catheter within a patient. For example, in some instances, the present disclosure is directed to a Foley catheter configured to introduce one or more fluorescent probes into a patient's urine drained via the catheter and including one or more sensors configured to facilitate detection and/or quantification of one or more physiological parameters of a patient's urine based on a fluorescence response of the fluorescent material in the urine to determine the health of the patient's kidneys (e.g., for renal monitoring). However, examples of the present disclosure are not limited to Foley-type catheters or urinary catheters.

As noted above, a Foley catheter may be a type of urinary catheter used in the examples of the present disclosure. A Foley catheter may be modified in the manner described herein to facilitate measurements of urine parameters for renal monitoring. In some examples, one or more sensors may be used in conjunction with a Foley catheter to monitor renal function to prevent acute kidney injury. In some examples, the sensor(s) may provide data indicating detection of and prevention of acute kidney injury.

FIG. 1 is a conceptual side elevation view of an example medical device 10, which includes an elongated body 12 and a hub 14. In some examples, medical device 10 may additionally include an anchoring member 18. In some examples, medical device 10 is a catheter, such as a Foley catheter. In other examples, medical device 10 may be configured to attach to catheter. While a Foley catheter and its intended use is primarily referred to herein to describe medical device 10, in other examples, medical device 10 may be used for other purposes, such as to drain wounds or for intravascular monitoring or medical procedures.

Medical device 10 includes a distal portion 17A and a proximal portion 17B. Distal portion 17A includes a distal end 12A of elongated body 12 and is intended to be external to a patient's body when in use, while proximal portion 17B includes a proximal end 12B of elongated body 12 and is intended to be internal to a patient's body when in use. For example, when proximal portion 17B is positioned within a patient, e.g., so proximal end 12B of elongated body 12 is within the patient's urethra and bladder, distal portion 17A may remain outside of the body of the patient.

As shown in FIG. 1, elongated body 12 may be a body extending from distal end 12A to proximal end 12B and defining one or more inner lumens. In the example shown in FIGS. 1 and 2, elongated body 12 defines lumen 34 and lumen 36 (shown in FIG. 2). In some examples, lumen 34 may be a drainage lumen for draining a fluid from a target site, such as a bladder. In other examples lumen 34 may be used for any other suitable purpose, such as a delivery lumen to deliver a substance or another medical device to a target site within a patient. Lumen 34 may extend from fluid opening 13 to fluid opening 14A. Both fluid opening 13 and fluid opening 14A may be fluidically coupled to lumen 34, so that a fluid may flow from one of fluid opening 13 or fluid opening 14A to the other of fluid opening 13 or fluid opening 14A through lumen 34. In the example where lumen 34 is a drainage lumen, fluid opening 13 and fluid opening 14A may be drainage openings. In the example shown in FIG. 1, distal end 12A of elongated body 12 is received within hub 14 and is mechanically connected to hub 14 via an adhesive, welding, or another suitable technique or combination of techniques.

In some examples, elongated body 12 has a suitable length for accessing the bladder of a patient through the urethra. The length may be measured along central longitudinal axis 16 of elongated body 12. In some examples, elongated body 12 may have an outer diameter of about 12 French to about 14 French, but other dimensions may be used in other examples. Distal and proximal portions of elongated body 12 may each have any suitable length.

Hub 14 is positioned at a distal end of elongated body 12 and defines an opening through which the one or more inner lumens (e.g., lumen 34 shown in FIG. 2) of elongated body 12 may be accessed and, in some examples, closed. While hub 14 is shown in FIG. 1 as having two arms, 14C and 14D, (e.g., a "Y-hub"), hub 14 may have any suitable number of arms, which may depend on the number of inner lumens defined by elongated body 12. For example, each arm may be fluidically coupled to a respective inner lumen of elongated body 12. In the example of FIG. 1, hub 14 comprises a fluid opening 14A, which is fluidically coupled to lumen 34, and an inflation opening 14B, which is fluidically coupled to an inflation lumen 36 (shown in FIG. 2) of elongated body 12. In examples in which anchoring member 18 does not include an expandable balloon, rather than defining inflation lumen 36, elongated body 12 may define an inner lumen configured to receive a deployment mechanism (e.g., a pull wire or a push wire) for deploying an expandable structure anchoring member 18 and hub 14 may comprise fluid opening 14A and an opening 14B via which a clinician may access the deployment mechanism.

In examples in which medical device 10 is a Foley catheter, a fluid collection container (e.g., a urine bag) may be attached to fluid opening 14A for collecting urine draining from the patient's bladder. In other examples, a catheter attachment 50 (e.g., illustrated in FIG. 3) may be attached to fluid opening 14A, and a fluid collection container may be attached to a subsequent fluid opening 54A in catheter attachment 50 for collecting urine draining from the patient's bladder. Inflation opening 14B may be operable to connect to an inflation device to inflate anchoring member 18 positioned on proximal portion 17B of medical device 10. Anchoring member 18 may be uninflated or undeployed when not in use. Hub 14 may include connectors, such as connector 15, for connecting to other devices, such as the fluid collection container, a catheter attachment, and the inflation source. For example, connector 15 may be at least a portion of a threaded fastener and include external threads for attaching to internal threads of another device. In some examples, medical device 10 includes strain relief member 11, which may be a part of hub 14 or may be separate from hub 14.

Proximal portion 17B of medical device 10 comprises anchoring member 18 and fluid opening 13. Anchoring member 18 may include any suitable structure configured to expand from a relatively low profile state to an expanded state in which anchoring member 18 may engage with tissue of a patient (e.g., inside a bladder) to help secure and prevent movement of proximal portion 17B out of the body of the patient. For example, anchoring member 18 may include an anchor balloon or other expandable structure. When inflated or deployed, anchoring member 18 may function to anchor medical device 10 to the patient, for example, within the patient's bladder. In this manner, the portion of medical device 10 on the proximal side of anchoring member 18 may not slip out of the patient's bladder. Fluid opening 13 may be positioned on the surface of longitudinal axis of medical device 10 between anchoring member 18 and the proximal end 12B (as shown) or may be positioned at the proximal end 12B.

In accordance with examples of the disclosure, medical device 10 may include one or more sensors configured to monitor one or more parameters of a fluid within lumen 34 (FIG. 2) of elongate body 12. In the example of FIG. 1, medical device 10 includes sensor 20. Sensor 20 may be configured to sense one or more parameters of a fluid in elongate body 12, e.g., of a fluid within lumen 34 of elongate body 12, as further described below. A variety of parameters of the fluid may be sensed by sensor 20 including, but not limited to, temperature, flow rate, luminescence, fluorescence, amount of oxygen, sound, flow velocity, density, specific gravity, and the like.

Sensor 20 may be configured to detect one or more fluid parameters of a fluid flowing through lumen 34 by detecting a fluorescence or fluorescence response of the fluorescent material in contact with fluid in lumen 34. As will be described below, fluorescent material fluoresces and/or emits a fluorescence response based on a fluid parameter. The fluorescence response may be detectable by a sensor, e.g., sensor 20. In some examples, the fluorescent material may respond to a stimulus (e.g., emitted light) in proportion to oxygen, e.g., an amount of oxygen or an oxygen concentration within the fluid.

The fluorescent material may include any material that fluoresces in response to exposure to light. For example, the fluorescent material may absorb light to reach an excited state and emit light at a lower wavelength to return to a relaxed state. A variety of fluorescent materials may be used including, but not limited to, platinum octaethylporphyrin (PtOEP), phosphors such as palladium (Pd)-porphyrin, PdTPTBP/PtTPTBP (e.g., palladium(ii)/platinum(ii) tetraphenyltetrabenzoporphyrin); Ir(Cs)$_2$acac (e.g., iridium(iii) bis-(benzothiazol-2-yl)-7-(diethylamino)-coumarin-(acetylacetonate)); and/or Ru-dpp (e.g., ruthenium(ii) tris-4,7-diphenyl-1,10-phenanthroline). In some materials, the rate at which the fluoresce fades is inversely proportional to the amount of oxygen it is exposed to. In such materials, the more oxygen present, the faster the fluorescence fades. By measuring the rate of fluorescence decay, sensor 20 may accurately measure the amount of oxygen in the fluid flowing within lumen 34, e.g., on a periodic or substantially continuous basis over a period of time.

Fluoresced light emitted by the fluorescent material may be dependent on the amount of excitation light received (e.g., an intensity of the excitation light), and measurement of the amount of fluorescence may be dependent on a fluorescent light detector view angle (e.g., angle of fluorescent light incident on the fluorescent light detector). In other words, measurement of the fluorescence of the fluorescent material may depend on the geometry of the components of sensor 20, e.g., the excitation light source position, angle, and output distribution, the position and geometry of the fluorescent material, the position and angle of the fluorescent light detector, the position and angle of any optics and/or lenses used to direct excitation light from the excitation light source to the fluorescent material and to direct fluorescent light from the fluorescent material to the fluorescent light detector. Additionally, measurements of the fluorescence of the fluorescent material may be affected by ambient light and interactions with background materials, e.g., bed sheets, gowns, skin, and/or any objects in the surrounding environment that may cause ambient light affecting sensor 20 and/or the fluorescent material.

According to examples described herein, medical device 10 may include a diffuse reflector (or an integrating sphere) to obtain a more accurate oxygen measurement. The diffuse reflector may be configured to receive light from one or more light sources, such as excitation light from an excitation light source or fluorescent light from a fluorescent light source, and scatter or diffuse the light to obtain a relatively spatially uniform light. For example, sensor 20 may include a diffuse reflector in the optical path between an excitation light source and the fluorescent material and/or between a fluorescent light detector and the fluorescent material. In some examples, medical device 10 may include a diffuse reflector configured to diffuse and direct excitation light from the excitation light source to the fluorescent material. For example, the diffuse reflector may be configured to receive excitation light from the excitation light source, diffuse the excitation light such to create a relatively uniform spatial distribution of the excitation light, and direct this diffused excitation light towards the fluorescent material. In some examples, medical device 10 may include a diffuse reflector configured to diffuse the diffuse reflector may be configured to receive fluoresced light from the fluorescent material, diffuse the fluoresced light to create a relatively uniform spatial distribution of the fluoresced light, and direct this diffuse fluoresced light towards a detector. Despite variations in various fluctuations in fluid flow that may cause scattering of light, the diffuse reflector may emit relatively spatially uniform excitation light and/or fluoresced light, such that the fluorescent material may receive a relatively uniform amount of light and/or the fluorescent light detector may receive a relatively uniform angle of light incident on the fluorescent light detector. In some examples, sensor 20 may include a housing configured to at least partially enclose the diffuse reflector(s) and/or a fluorescent material within the fluid. The diffuse reflector may be made of any suitable diffusely reflecting material at the excitation and fluorescence wavelengths, for example, flat white paint, barium sulfate (BaSO4), Spectralon®, polytetrafluoroethylene (PTFE), Teflon®, and the like. In some examples, sensor 20 may include a fluorescent material within an integrating sphere having inner walls made of a diffuse reflecting material.

Sensor 20 may be positioned on distal portion 17A of elongated body 12 of medical device 10 including portions of elongated body 12 positioned distal to distal end 12A connected to a fluid collection container (e.g., a urine bag) or the like. In some examples, sensor 20 is mechanically connected to elongated body 12 or another part of medical device 10 using any suitable technique, such as, but not limited to, an adhesive, welding, by being embedded in elongated body 12, via a crimping band or another suitable attachment mechanism or combination of attachment mechanisms. Sensor 20 may be removably coupled to elongated body 12. That is, sensor 20 may be coupled to elongated body 12 and used for a procedure and then sensor 20 may be removed, coupled to another elongated body and used again. In some examples, elongated body 12 includes a structure distal to a distal end of medical device 10, such as tubing extending between hub 14 and a fluid collection container, which sensor 20 may be coupled to.

In some examples, sensor 20 may be disposable and/or reusable. In some examples, sensor 20 may be disposed of, such as placed into medical waste, when elongated body 12 is through being used for a medical procedure. In some examples, all or a portion of sensor 20 may be reusable and detachable from elongated body 12 so sensor 20, or a portion thereof, may be used again on another elongated body for the same, similar or different procedure. For purposes of the disclosure disposable may be defined as an article intended to be used once, or until no longer useful, and then thrown away. Reusable may be defined as an item which can be used again or more than once. A reusable sensor may be configured such that sensor may be coupled to elongate body 12 so that it functions as described in the examples of the disclosure, subsequently removed from elongate body 12 and then coupled to another elongate body in a manner that allows the sensor to again function as described herein on the other elongated body.

In some examples, sensor 20 may configured as a reusable sensor that may be used with multiple different catheters. For example, one or more components of sensor 20 may be removably coupled to elongate body 12 so that those components may be removed from elongated body, e.g., when medical device 10 is removed from a patient, and then removably coupled to a similar medical device to function in the same or similar manner as an ultrasonic flow sensor. In this manner, one or more relatively expensive components of sensor 20 may be used with multiple catheters rather than using those components in a single use manner with one catheter.

Sensor 20 may be configured to sense or otherwise monitor a composition of a fluid (e.g., an amount or concentration of oxygen within the fluid) within elongated body 12 using a fluorescence lifetime technique. Oxygen may be sensed using a fluorescence lifetime technique. A fluorescence (or luminescence) material may be exposed to a certain wavelength or range of wavelengths (i.e. absorption spectrum) of light and absorb the light to enter an excited state. In response to enter this excited state, the fluorescent material may fluoresce by emitting light at certain wavelengths (i.e. emission spectrum) to enter a relaxed state. In certain materials, the rate at which the intensity of the fluorescence fades may be inversely proportional to the amount of oxygen in the surrounding fluid. For example, oxygen molecules may quench the fluorescence response, such that increase in an amount or concentration of oxygen may correspond to an increase in a rate of fading of the fluorescence response (i.e., a rate of fluorescence decay). As such, by measuring the rate of fluorescence decay, sensor 20 may measure an amount or concentration of oxygen in the fluid.

Sensor 20 may be configured to stimulate and measure a fluorescence response in the fluorescent material. For example, sensor 20 may include a light source configured to emit light to expose the fluorescent material to the emitted light. In such a configuration, the fluorescent material within the fluid may fluoresce when exposed to the light in lumen 34. Sensor 20 may also include a light detector configured to detect the fluorescence of the fluorescent material. Sensor 20 may be configured to detect oxygen in the fluid within lumen 34 based on the detected fluorescence. For example, the fluorescent material may glow or fluoresce when exposed to the light. In some materials, the rate at which the fluoresce fades is inversely proportional to the amount of oxygen it is exposed to. In such materials, the more oxygen present, the faster the fluorescence fades. By measuring the rate of fluorescence decay, sensor 20 may accurately measure the amount of oxygen in the fluid flowing within lumen 34, e.g., on a periodic or substantially continuous basis over a period of time.

Sensor 20 may communicate sensor data to external device 24 via an electrical, optical, wireless or other connection. In some examples, sensor 20 may communicate sensor data to external device 24 through a connection(s) within elongated body 12 of medical device 10 from proximal portion 17B to distal portion 17A via embedded wire(s) or optical cable(s). In other examples, sensor 20 may communicate sensor data to external device 24 via a wireless communication technique.

External device 24 may be a computing device, such as a workstation, a desktop computer, a laptop computer, a smart phone, a tablet, a server or any other type of computing device configured to receive, process and/or display sensor data. Sensor 20 may communicate sensor data to the external device via a connection 26. Connection 26 may be an electrical, optical, wireless or other connection.

Many sensors require calibration information to be accurate. Sensors may provide increasingly accurate measurements with sensor-specific calibration information to compensate for variability in the sensors. For example, a fluorescence lifetime oxygen sensor may have calibration parameters related to the fluorescing material used, as well as the specifics of the light source and light detector.

Sensor 20 may use calibration information to increase an accuracy of measurements. Flow sensors and oxygen sensors may use sensor-specific calibration information to produce an accurate measurement and compensate for variability in sensor 20. For example, a fluorescent material may be temperature-dependent and therefore to obtain a more accurate oxygen measurement it may be helpful to know the temperature of the fluid. Sensor 20 may include additional sensors, e.g., one or more temperature sensors configured to determine a temperature of the fluid. In some examples, medical device 10 may include one or more temperature sensors at other locations along elongated body 12, e.g., spaced from sensor 20 rather than included with sensor 20. The one or more temperature sensors may be upstream or downstream from sensor 20, or near sensor 20, or included with sensor 20, and may be used as the reference for the temperature of the fluid.

Sensor 20 may have memory on sensor 20 that stores sensor calibration information, which may be used, e.g., by external device 24, to more accurately read sensor data being sent from sensor 20. Additionally, or alternatively, medical device 10 may include memory 19 and memory 19 may store sensor calibration information to calibrate sensor 20 based on the sensor calibration information stored by memory 19. Through including the sensor calibration in the sensor or memory 19 accuracy of the measurement may increase. Further, the ability to change components in a sensor or offer different ranges of sensors in the future without changing the monitoring software may provide flexibility.

Memory 19 may be located on elongated body 12 or hub 14. In some examples, all or a portion of memory 19 may be removable from elongated body 12 and may be located on or adjacent with sensor 20. Data sensed by sensor 20 may be stored on memory 19, e.g., for later retrieval by external device 24 and/or for processing of the sensor data from sensor 20. While memory 19 is shown as being separate from sensor 20, in some examples, sensor 20 may additionally or alternatively include another memory for storing data from sensor 20.

In some examples, memory 19 may include all or a portion of calibration data for sensor 20. Processing circuitry may store sensor data within memory 19 and communicate this data with external device 24. In some examples, medical device 10 may have processing circuitry on elongated body 12 or hub 14 that may control all or some operations of sensor 20. In some examples, the processing circuitry of external device 24 may control all or some operations of sensor 20. In some examples, the processing circuitry of external device 24 and processing circuitry of medical device 10 may control all or some of operations of sensor 20 together. Memory 19 may also store calibration information for sensor 20. This calibration information may assist in providing calibration information to sensor 20 and thus improve the collecting of more accurate information from sensor 20. Memory 19 may also receive information from external device 24, which memory 19 may retain onboard after disconnection from external device 24. Further, memory 19 may then share this information with another external device in the event external device 24 breaks down or in the more likely event the patient to whom medical device 10 is inserted into may be moved from surgery to an intensive care. In intensive care, memory 19 may now communicate with another external device and share information collected from surgery.

Memory 19 may store program instructions, such as software or algorithms, which may include one or more program modules, which are executable by processing circuitry (not shown in FIG. 1). When executed by the processing circuitry, such program instructions may cause the processing circuitry and external device 24 to provide the functionality ascribed to them herein. The program instructions may be embodied in software and/or firmware. Memory 19 may include any volatile, non-volatile, magnetic, optical, or electrical media, such as a random access memory (RAM), read-only memory (ROM), non-volatile RAM (NVRAM), electrically erasable programmable ROM (EEPROM), flash memory, or any other digital media.

Elongated body 12 may be structurally configured to be relatively flexible, pushable, and relatively kink- and buckle-resistant, so it may resist buckling when a pushing force is applied to a relatively distal portion of medical device 10 to advance elongated body 12 proximally through the urethra and into the bladder. Kinking and/or buckling of elongated body 12 may hinder a clinician's efforts to push the elongated body proximally. Any suitable material may be used for elongated body 12, such as a suitable biocompatible polymer or other biocompatible material.

Figure 2:
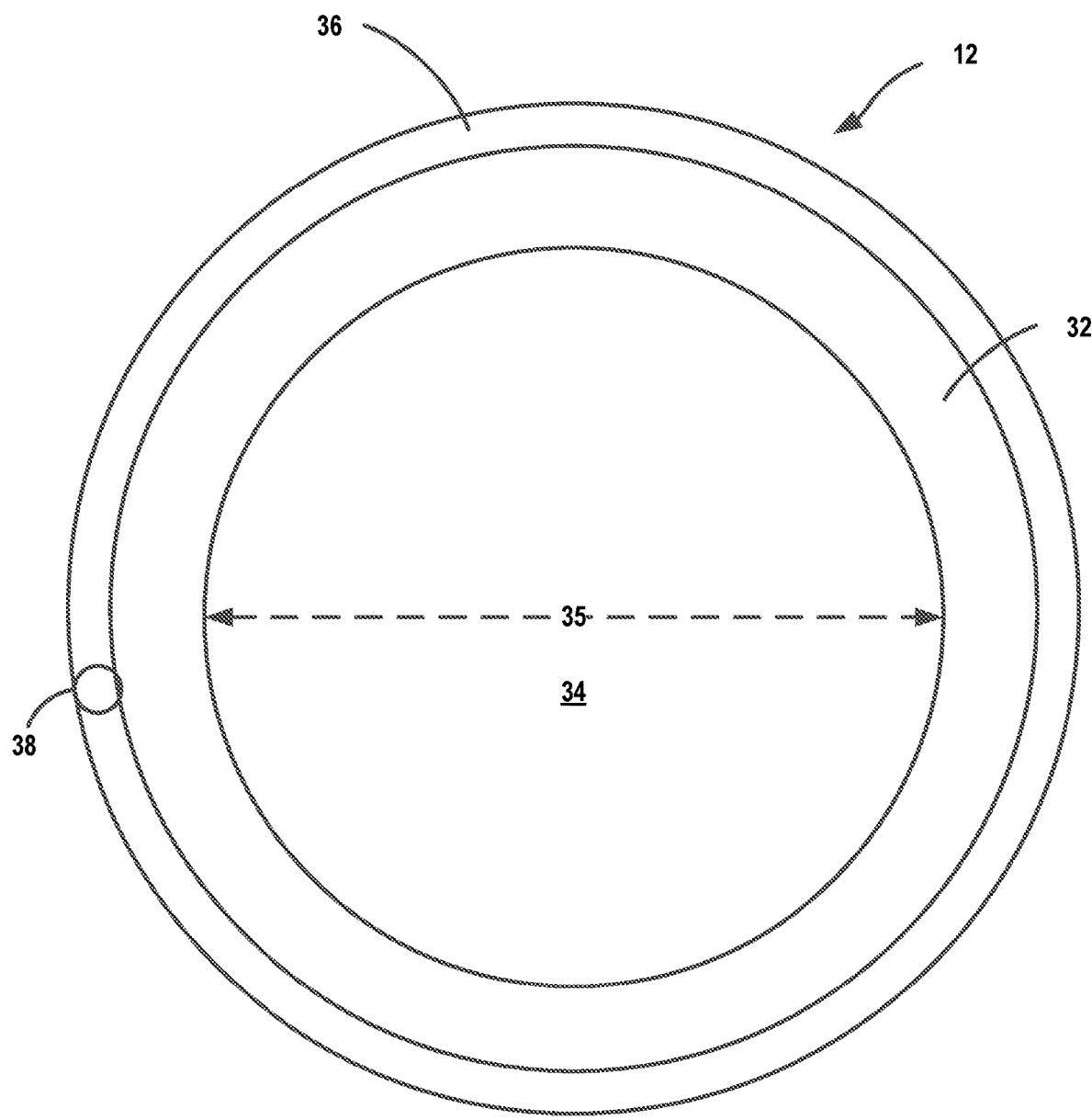
FIG. 2 is a diagram illustrating example a cross-section taken along line 1-1 of the medical device of FIG. 1 according to the techniques of this disclosure.

FIG. 2 is a diagram illustrating an example cross-section of medical device 10, where the cross-section is taken along line 1-1 in FIG. 1 in a direction perpendicular to central longitudinal axis 16. FIG. 2 depicts a cross section of elongated body 12, which defines lumen 34 and lumen 36. In some examples, lumen 34 may be referred to as a drainage lumen, such as in examples in which medical device 10 is a Foley catheter configured to drain urine from a bladder of a patient, and lumen 36 may be referred to as an inflation lumen in examples in which lumen 36 is configured to deliver an inflation fluid to anchoring member 18. Elongated body 12 may enclose connection 38.

Lumen 34 may serve as a passage for urine entering medical device 10 through fluid opening 13 to fluid opening 14A. In the example shown in FIG. 2, lumen wall 32 is relatively non-permeable to substances of interest, such as oxygen and/or carbon dioxide, and positioned between lumen 36 and lumen 34. In some examples, lumen wall 32 extends along an entire length of lumen 34, while in other examples, lumen wall 32 extends along a part of a length of lumen 34, for example, from a portion of lumen 34 intended to be in a patient's bladder during use, which may help maintain a desired level of flexibility of elongated body 12. In addition, as shown in FIG. 2, in some examples, lumen wall 32 extends around an entire outer perimeter of lumen 34 (e.g., an outer circumference in examples in which the inner perimeter is circular in cross-section).

Inflation lumen 36 may serve as a passage for a fluid, such as sterile water or saline, or a gas, such as air, from inflation opening 14B to anchoring mechanism 18. For example, an inflation device (not shown) may pump fluid or gas into inflation lumen 36 through inflation opening 14B into anchoring member 18 so anchoring member 18 is inflated to a size suitable to anchor medical device 10 to the patient's bladder. While inflation lumen 36 is shown as circular in cross section, it may be of any shape. In some examples, there may be a plurality of inflation lumens. For example, a plurality of inflation lumens may substantially surround lumen 34. In some examples, anchoring member 18 may be an expandable structure not an inflatable balloon. In such examples, inflation lumen 36 may be replaced by a deployment mechanism which may permit a clinician to expand the expandable structure. For example, inflation lumen may be replaced by a mechanical device pushed and pulled separately from the medical device 10 by a clinician to expand or retract the expandable structure.

Connection 38 may serve to connect sensor 20 positioned at distal portion 17A to connection 26 and/or memory 19. Connection 38 may be an electrical, optical or other connection. In some examples, connection 38 may comprise a plurality of connections. For example, connection 38 may include one of more wired or optical connections to a temperature sensor and one or more connections to a pressure sensor. In some examples, connection 38 may include one or more power connections in order to provide power to sensor 20 and one or more communications connections to receive sensor data from sensor 20 and to receive calibration information from memory 19.

In examples of the disclosure, lumen 34 may have a small diameter 35 to increase the transit time of the fluid within lumen 34. In some Foley Catheters, the drainage lumen cross-sectional area may be maximized to maximize the flow rate. Adult Foley Catheters may be, e.g., 12, 14, or 16 French (e.g., with a drainage lumen diameter of about 1.3 mm to about 2.6 mm). For a given flow rate, as the cross-sectional area increases the transit time of fluid through lumen 34 decreases. Drainage lumen 34 may have a relatively small cross-sectional area, e.g., to decrease the flow rate and increase fluid transit time. Through increasing the transit time, physical characteristics of the fluid (e.g., oxygen, temperature, etc.) are preserved which increases the accuracy and utility of measurements. In some examples, diameter 35 may be about 0.75 mm to about 1.25 mm. A small inner diameter 35 of lumen 34 with an increased wall diameter (e.g., thicker walls 32) may contribute to the preservation of sensor measurements by also decreasing the gas permeability of elongated body 12. Further, the diameter of lumen 34 may be continuous over the length of elongate body 12 or it may vary. In some examples, medical device 10 may include sensor 20 including a diffuse reflector. In some examples, the lumen diameter may be configured such that at least a portion of sensor 20 may fit or otherwise be disposed within lumen 34. In some examples, the lumen diameter may be tailored based on the location of sensor 20, e.g., to increase the accuracy of the measurement by modifying or otherwise controlling the transit time of the fluid relative to the location at which sensor 20 is sensing the fluid. For example, lumen 34 may decrease in diameter relative to the location of sensor 20 so that the transit time of the fluid decreases in the area that sensor 20 is sensing the fluid. In some examples, a narrow lumen may expand the diameter at a sensor location on the elongated body of the catheter. This expansion of the diameter may increase sensor sensitivity and accuracy by increasing the time the fluid spends at the sensor location.

Figure 3:
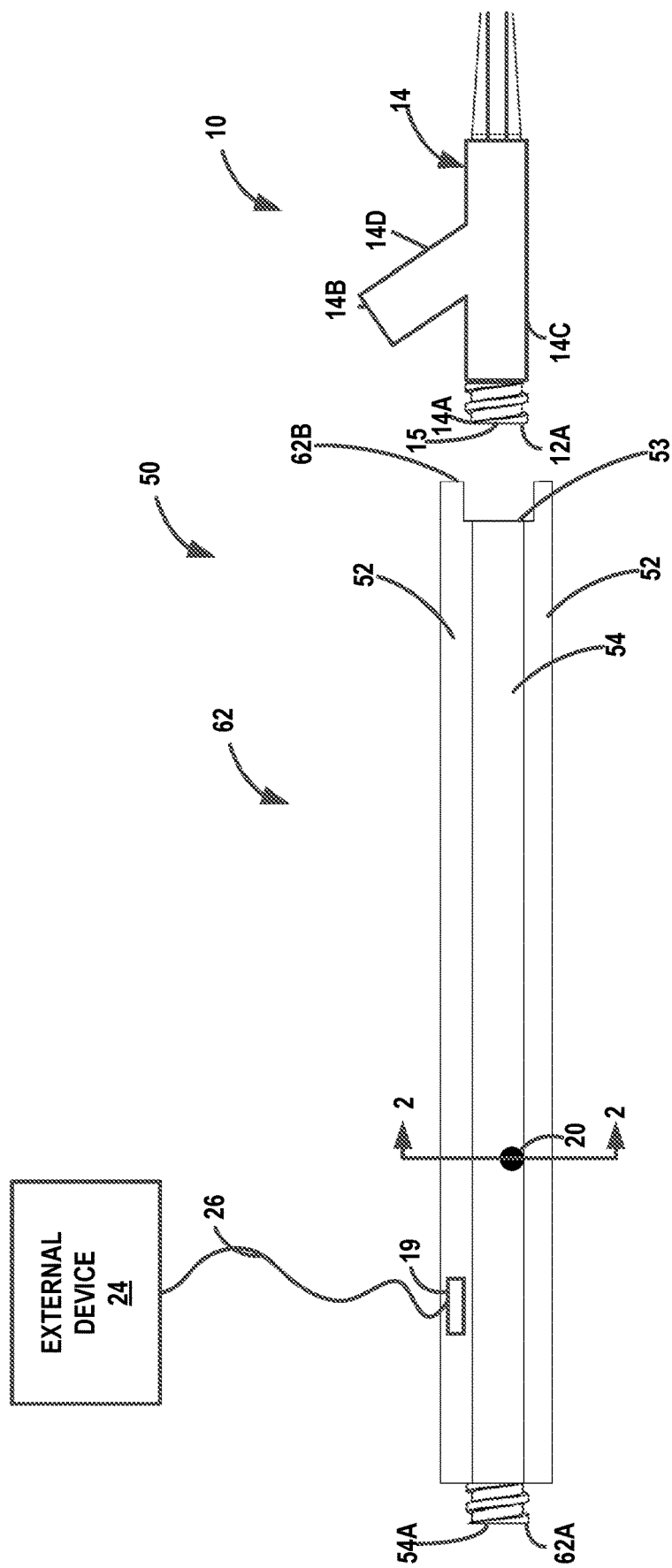
FIG. 3 is a diagram illustrating another example medical device, in accordance with one or more techniques of this disclosure.

In some instances, medical devices described herein may attach to an existing medical device for providing additional sensing functionality to the medical device. FIG. 3 is a diagram illustrating another example medical device 50, in accordance with one or more techniques of this disclosure. FIG. 3 is a conceptual side elevation view of medical device 50. In some examples, medical device 50 may be a catheter attachment configured to attach to a catheter, such as a Foley catheter. In the example of FIG. 3, medical device 50 may be configured to attach to a medical device 60. For example, connector 55 of medical device 50 may include internal threads which may receive external threads of connector 15 of medical device 60, such as described with reference to medical device 10 of FIG. 1 and reproduced in part in FIG. 3. In other examples, medical device 50 may attach to a catheter by any suitable means such that fluid from the catheter may flow into lumen 54 through fluid opening 53 of medical device 50, e.g., from fluid opening 14A at distal end 12A of medical device 60.

As shown in FIG. 3, elongated body 62 may be a body extending from distal end 62A to proximal end 62B and that defines inner lumen 54. For example, elongated body 62 defines lumen 54, which may be substantially similar to lumen 34 as illustrated in FIG. 2. In some examples, lumen 54 may be fluidically connected to lumen 34 and serve as an extension to lumen 34. Lumen 54 may extend from fluid opening 53 to fluid opening 54A. Both fluid opening 53 and fluid opening 54A may be fluidically coupled to lumen 54, so that a fluid may flow from one of fluid opening 53 or fluid opening 54A to the other of fluid opening 53 or fluid opening 54A through lumen 54. In some examples, a fluid collection container (e.g., a urine bag) may be attached to fluid opening 54A for collecting urine draining from the patient's bladder. In some examples, elongated body 62 may have an outer diameter substantially similar to elongated body 12 but may have other dimensions in other examples.

In accordance with examples of the disclosure, medical device 50 may include one or more sensors which may be configured to monitor one or more parameters of a fluid within lumen 54 of elongate body 62. For example, in FIG. 3, medical device 50 includes sensor 20. As described above with reference to medical device 10, sensor 20 may be configured to sense one or more parameters, such as a temperature, flow rate, luminescence, fluorescence, amount of oxygen, sound, flow velocity, density, specific gravity, and the like.

Sensor 20 may be configured to detect one or more fluid parameters of a fluid flowing through lumen 54 by detecting a fluorescence or fluorescence response of the fluorescent material in contact with fluid in lumen 54, as described above with respect to FIG. 1. Fluorescent material fluoresces and/or emits a fluorescence response based on a fluid parameter. The fluorescence response may be detectable by a sensor, e.g., sensor 20. In some examples, the fluorescent material may respond to a stimulus (e.g., emitted light) in proportion to oxygen, e.g., an amount of oxygen or an oxygen concentration within the fluid.

The fluorescent material may include any material that fluoresces in response to exposure to light. For example, the fluorescent material may absorb light to reach an excited state and emit light at a lower wavelength to return to a relaxed state. A variety of fluorescent materials may be used including, but not limited to, platinum octaethylporphyrin (PtOEP), phosphors such as palladium (Pd)-porphyrin, PdTPTBP/PtTPTBP (e.g., palladium(ii)/platinum(ii) tetraphenyltetrabenzoporphyrin); Ir(Cs)$_2$acac (e.g., iridium(iii) bis-(benzothiazol-2-yl)-7-(diethylamino)-coumarin-(acetylacetonate)); and/or Ru-dpp (e.g., ruthenium(ii) tris-4,7-diphenyl-1,10-phenanthroline). In some materials, the rate at which the fluoresce fades is inversely proportional to the amount of oxygen it is exposed to. In such materials, the more oxygen present, the faster the fluorescence fades. By measuring the rate of fluorescence decay, sensor 20 may accurately measure the amount of oxygen in the fluid flowing within lumen 34, e.g., on a periodic or substantially continuous basis over a period of time.

Fluoresced light emitted by the fluorescent material may be dependent on the amount of excitation light received (e.g., an intensity of the excitation light), and measurement of the amount of fluorescence may be dependent on a fluorescent light detector view angle (e.g., angle of fluorescent light incident on the fluorescent light detector). In other words, measurement of the fluorescence of the fluorescent material may depend on the geometry of the components of sensor 20, e.g., the excitation light source position, angle, and output distribution, the position and geometry of the fluorescent material, the position and angle of the fluorescent light detector, the position and angle of any optics and/or lenses used to direct excitation light from the excitation light source to the fluorescent material and to direct fluorescent light from the fluorescent material to the fluorescent light detector. Additionally, measurements of the fluorescence of the fluorescent material may be affected by ambient light and interactions with background materials, e.g., bed sheets, gowns, skin, and/or any objects in the surrounding environment that may cause ambient light affecting sensor 20 and/or the fluorescent material.

According to examples described herein, medical device 50 may include a diffuse reflector (or an integrating sphere) to obtain a more accurate oxygen measurement. The diffuse reflector may be configured to receive light from one or more light sources, such as excitation light from an excitation light source or fluorescent light from a fluorescent light source, and scatter or diffuse the light to obtain a relatively spatially uniform light. For example, sensor 20 may include a diffuse reflector in the optical path between an excitation light source and the fluorescent material and/or between a fluorescent light detector and the fluorescent material. In some examples, medical device 50 may include a diffuse reflector configured to diffuse and direct excitation light from the excitation light source to the fluorescent material. For example, the diffuse reflector may be configured to receive excitation light from the excitation light source, diffuse the excitation light such to create a relatively uniform spatial distribution of the excitation light, and direct this diffused excitation light towards the fluorescent material. In some examples, medical device 50 may include a diffuse reflector configured to diffuse the diffuse reflector may be configured to receive fluoresced light from the fluorescent material, diffuse the fluoresced light to create a relatively uniform spatial distribution of the fluoresced light, and direct this diffuse fluoresced light towards a detector. Despite variations in various fluctuations in fluid flow that may cause scattering of light, the diffuse reflector may emit relatively spatially uniform excitation light and/or fluoresced light, such that the fluorescent material may receive a relatively uniform amount of light and/or the fluorescent light detector may receive a relatively uniform angle of light incident on the fluorescent light detector. In some examples, sensor 20 may include a housing configured to at least partially enclose the diffuse reflector(s) and/or a fluorescent material within the fluid. The diffuse reflector may be made of any suitable diffusely reflecting material at the excitation and fluorescence wavelengths, for example, flat white paint, barium sulfate (BaSO4), Spectralon®, polytetrafluoroethylene (PTFE), Teflon®, and the like. In some examples, sensor 20 may include a fluorescent material within an integrating sphere having inner walls made of a diffuse reflecting material.

Sensor 20 may be positioned along elongated body 62 of medical device 50, including portions of elongated body 62 positioned distal to distal end 62A connected to a fluid collection container (e.g., a urine bag) or the like. In some examples, sensor 20 is mechanically connected to elongated body 62 or another part of medical device 50 using any suitable technique, such as, but not limited to, an adhesive, welding, by being embedded in elongated body 62, via a crimping band or another suitable attachment mechanism or combination of attachment mechanisms. Sensor 20 may be removably coupled to elongated body 62. That is, sensor 20 may be coupled to elongated body 62 and used for a procedure and then sensor 20 may be removed, coupled to another elongated body and used again. In some examples, elongated body 62 includes a structure distal to a distal end of medical device 50, such as tubing extending distal end 62A and a fluid collection container, which sensor 20 may be coupled to.

In some examples, sensor 20 may be disposable and/or reusable, such as described with respect to FIG. 1 above. Sensor 20 may be configured to sense or otherwise monitor a composition of a fluid (e.g., an amount or concentration of oxygen within the fluid) within elongated body 62 using a fluorescence lifetime technique, such as described above with respect to FIG. 1 and with reference to elongated body 12.

As described above, sensor 20 may communicate sensor data to external device 24 via an electrical, optical, wireless or other connection. In some examples, sensor 20 may communicate sensor data to external device 24 through a connection(s) within elongated body 62 of medical device 50 via embedded wire(s) or optical cable(s). In other examples, sensor 20 may communicate sensor data to external device 24 via a wireless communication technique. In some examples, and similar to as described above, sensor 20 may require calibration, and may have memory that stores sensor calibration information. Additionally, or alternatively, medical device 50 may include memory 19 and memory 19 may store sensor calibration information to calibrate sensor 20 based on the sensor calibration information stored by memory 19. Through including the sensor calibration in the sensor or memory 19 accuracy of the measurement may increase. Further, the ability to change components in a sensor or offer different ranges of sensors in the future without changing the monitoring software may provide flexibility.

Memory 19 may be located on elongated body 62. In some examples, all or a portion of memory 19 may be removable from elongated body 62 and may be located on or adjacent with sensor 20. Data sensed by sensor 20 may be stored on memory 19, e.g., for later retrieval by external device 24 and/or for processing of the sensor data from sensor 20. While memory 19 is shown as being separate from sensor 20, in some examples, sensor 20 may additionally or alternatively include another memory for storing data from sensor 20.

In some examples, memory 19 may include all or a portion of calibration data for sensor 20. Processing circuitry may store sensor data within memory 19 and communicate this data with external device 24. In some examples, medical device 50 may have processing circuitry on elongated body 62 that may control all or some operations of sensor 20. In some examples, the processing circuitry of external device 24 may control all or some operations of sensor 20. In some examples, the processing circuitry of external device 24 and processing circuitry of medical device 50 may control all or some of operations of sensor 20 together. Memory 19 may also store calibration information for sensor 20. This calibration information may assist in providing calibration information to sensor 20 and thus improve the collecting of more accurate information from sensor 20. Memory 19 may also receive information from external device 24, which memory 19 may retain onboard after disconnection from external device 24. Further, memory 19 may then share this information with another external device in the event external device 24 breaks down or in the more likely event the patient to whom medical device 50 is attached may be moved from surgery to an intensive care. In intensive care, memory 19 may now communicate with another external device and share information collected from surgery.

As described above, memory 19 may store program instructions, such as software or algorithms, which may include one or more program modules, which are executable by processing circuitry (not shown in FIG. 1). When executed by the processing circuitry, such program instructions may cause the processing circuitry and external device 24 to provide the functionality ascribed to them herein. The program instructions may be embodied in software and/or firmware. Memory 19 may include any volatile, non-volatile, magnetic, optical, or electrical media, such as a random access memory (RAM), read-only memory (ROM), non-volatile RAM (NVRAM), electrically erasable programmable ROM (EEPROM), flash memory, or any other digital media.

Elongated body 62 may be structurally configured to be relatively flexible, pushable, and relatively kink- and buckle-resistant, so it may resist buckling when a pushing force is applied to a relatively distal portion of medical device 50. Any suitable material may be used for elongated body 62, such as a suitable biocompatible polymer or other biocompatible material.

Figure 4:
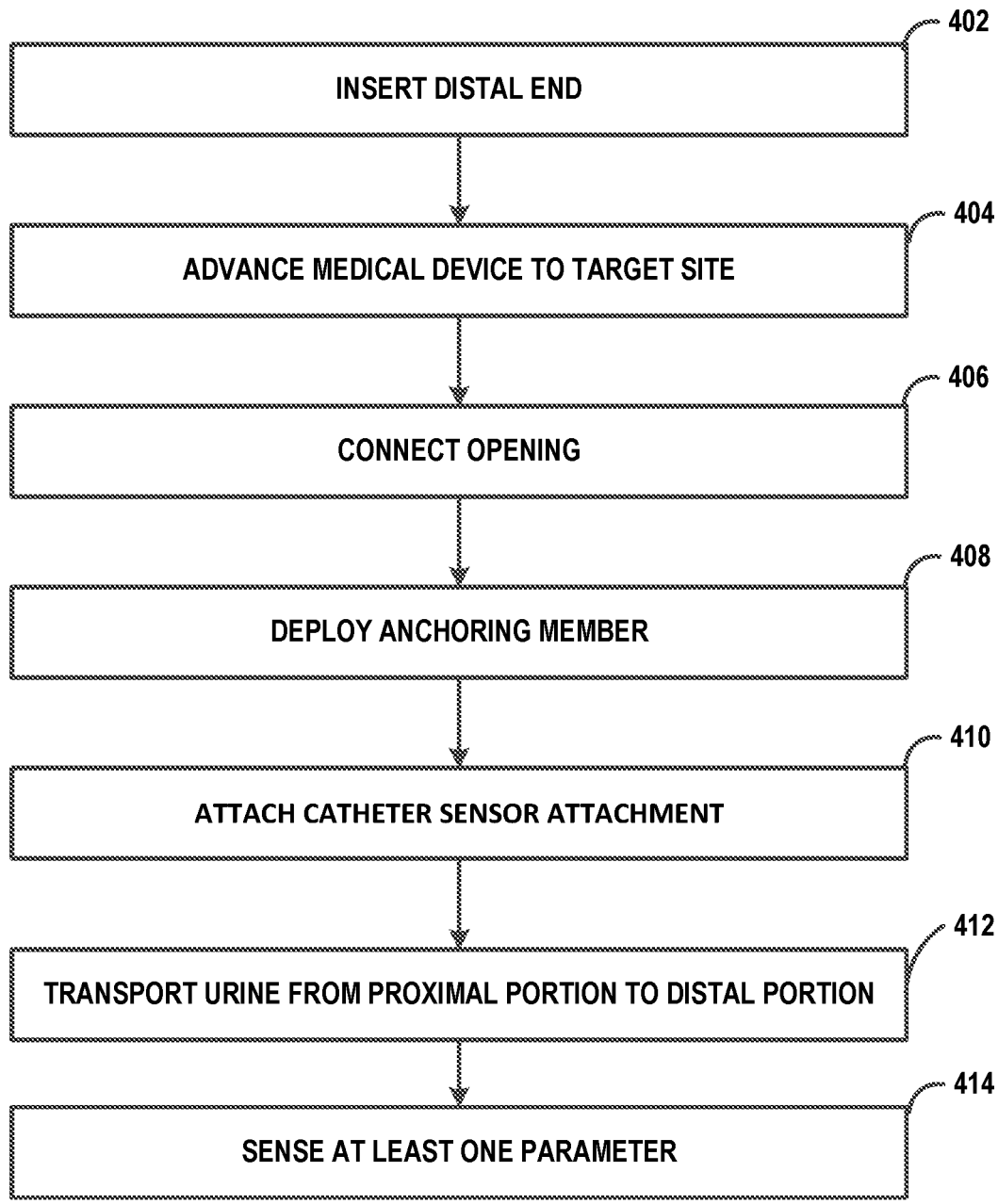
FIG. 4 is a flowchart illustrating an example method of operating a medical device according to the techniques of this disclosure.

Medical devices described herein, such as medical device 10 and/or medical device 50, may be used by a clinician to sense one or more parameters of a fluid in a patient. FIG. 4 is a flowchart illustrating an example operation of medical device 10 and/or medical device 50. A clinician may insert proximal end 12B of medical device 10 into a patient's urethra (402). The clinician may advance medical device 10 through the patient to a target site (404), e.g., until uninflated or undeployed anchoring member 18 is within the patient's bladder (404). The clinician may connect inflation opening 14B to an inflation device and may connect fluid opening 14A to a fluid collection container and/or to external sensors (406). The clinician may then deploy anchoring member 18 to help secure medical device 10 relative to the target site (408). For example, the clinician may inflate anchoring member 18, for example, using an inflation device and inflation fluid, such as sterile water, saline, or a gas. In examples in which anchoring member 18 is an expandable structure, the clinician may deploy anchoring member 18 by pushing a structure radially outwards or pulling back on a structure to cause the expandable structure to expand radially outwards.

Optionally, a clinician may attach medical device 50 to a catheter, e.g., a Foley catheter used rather than medical device 10 (410). For example, the clinician may screw medical device 50 onto a distal end of a Foley catheter, or attach medical device to the catheter by any suitable means such that lumen 54 is in fluid communication with the lumen of the catheter configured to drain urine from the patient. In some example, attachment of medical device 50 may be done prior to deploying anchoring member, connecting inflation opening, or inserting and advancing the catheter to a target site.

Lumen 34 of medical device 10 may transport urine from the proximal portion 17B of medical device 10 to the distal portion 17A of medical device 10 (412). Sensor 20 may sense at least one parameter, such as temperature and/or oxygen, from urine being transported through lumen 34 (414). For example, sensor 20 may sense a parameter such as urine flow (e.g., fluid velocity or volume), and/or amount of dissolved oxygen in the urine. In some examples, sensor 20 may sense at least one parameter between medical device 10 and a fluid collection container, e.g., at the distal end of elongate body 12.

Additionally or alternatively, lumen 54 of medical device 50 may transport urine from the proximal end 62B of medical device 50 to the distal 62A of medical device 50 (412). Sensor 20 may sense at least one parameter, such as temperature and/or oxygen, from urine being transported through lumen 54 (414). For example, sensor 20 may sense a parameter such as an amount of dissolved oxygen in the urine. In some examples, sensor 20 may sense at least one parameter between medical device 50 and a fluid collection container, e.g., at the distal end of elongate body 62.

While the example of FIG. 4, sets forth a number of steps, these steps may be performed in a different order or concurrently. For example, the clinician may connect the inflation opening 14B to an inflation device and/or may connect fluid opening 14A to a fluid collection container and/or to sensor 20 prior to inserting the proximal end 12B of medical device 10 into the patient's urethra and lumen 34 may transport urine concurrently with sensor 20 sensing any parameters.

Figure 5:
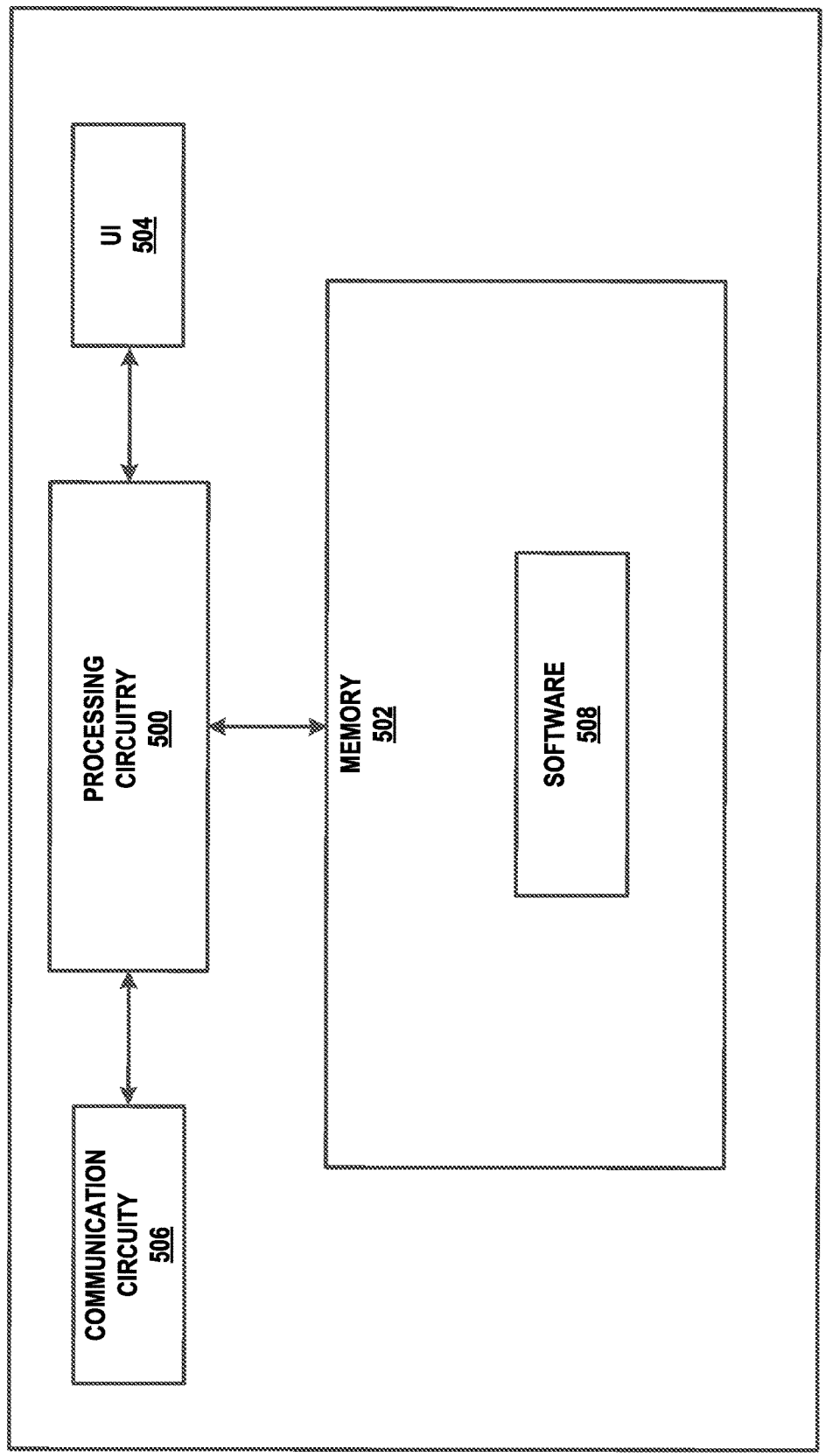
FIG. 5 is a block diagram of an example external device used with a medical device according to the techniques of this disclosure.

Medical devices described herein, such as medical device 10 and/or medical device 50, may communicate with one or more external devices, such as by receiving control signals and/or sending measurement signals. FIG. 5 is a functional block diagram illustrating an example of an external device 24 configured to communicate with sensor 20, receive information from sensor 20 and store and retrieve information from memory 19. In the example of FIG. 5, external device 24 includes processing circuitry 500, memory 502, user interface (UI) 504, and communication circuitry 506. External device 24 may be a dedicated hardware device with dedicated software for reading sensor data. Alternatively, external device 24 may be an off-the-shelf computing device, e.g., a desktop computer, a laptop computer, a tablet, or a smartphone running a mobile application enabling external device 24 to read sensor data from sensor 20 and memory 19.

In some examples, a user of external device 24 may be clinician, physician, intensivist, or heath care giver. In some examples, a user uses external device 24 to monitor a patient's kidney function, e.g., based on information sensed by sensor 20 or otherwise derived from information sensed by sensor 20 in the manner described herein. In some examples, the user may interact with external device 24 via UI 504, which may include a display to present a graphical user interface to the user, and a keypad or another mechanism (such as a touch sensitive screen) for receiving input from the user. External device 24 may communicate with sensor 20 and/or memory 19 using wired, wireless or optical methods through communication circuitry 506.

Processing circuitry 500 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 500 may include multiple components, such as any combination of one or more microprocessors, one or more DSPs, one or more ASICs, or one or more FPGAs, as well as other discrete or integrated logic circuitry, and/or analog circuitry.

Memory 502 may store program instructions, such as software 508, which may include one or more program modules, which are executable by processing circuitry 500. When executed by processing circuitry 500, such program instructions may cause processing circuitry 500 and external device 24 to provide the functionality ascribed to them herein. The program instructions may be embodied in software and/or firmware. Memory 502 may include any volatile, non-volatile, magnetic, optical, or electrical media, such as a random access memory (RAM), read-only memory (ROM), non-volatile RAM (NVRAM), electrically erasable programmable ROM (EEPROM), flash memory, or any other digital media.

FIGS. 6-10 illustrate various arrangements of fluorescence sensors and techniques for operating the fluorescence sensors. The fluorescence sensors of FIGS. 6-9 may interface with external device 24 of FIG. 5, and the techniques of FIG. 10 may be at least partially performed by external device 24 of FIG. 5.

Figure 6:
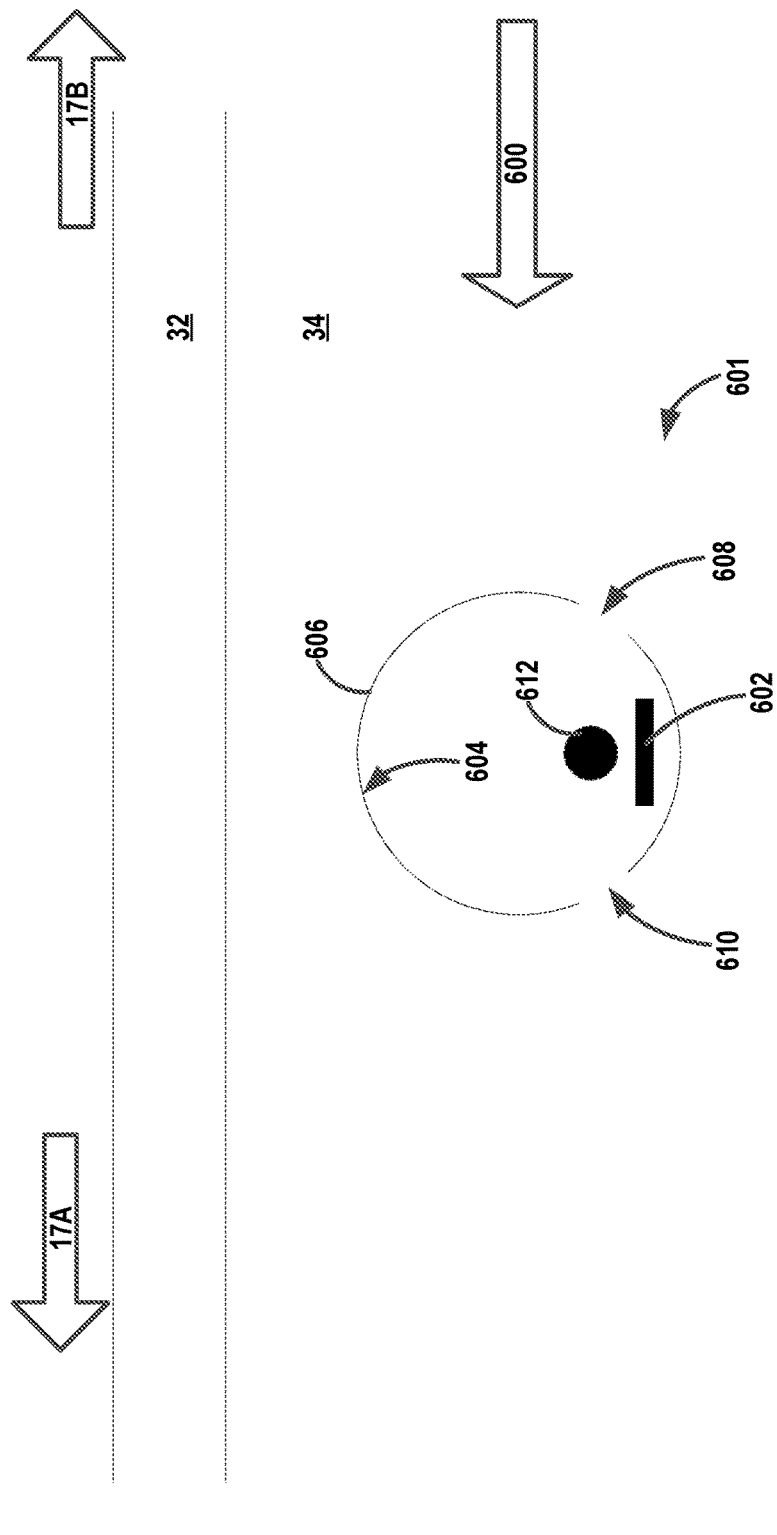
FIG. 6 is a diagram illustrating an example sensor used with a medical device according to the techniques of this disclosure.

FIG. 6 is a diagram illustrating an example fluorescence sensor 601 used with a medical device 10 and/or a medical device 50, according to the techniques of this disclosure. Fluorescence sensor 601 may be an example of sensor 20 of medical device 10 (FIG. 1) and/or medical device 50 (FIG. 3), and fluorescence sensor 601 may be used in place of sensor 20, used in combination with sensor 20 and other sensors such as temperature sensors, or in addition to sensor 20 and other sensors such as temperature sensors. In the example shown, fluid 600 is flowing from proximal portion 17B to distal portion 17A of medical device 10, as indicated by the directional arrow. Additionally or alternatively, fluid 600 may flow from proximal end 62B to distal end 62A of medical device 50.

Fluorescence sensor 601 may be configured to determine an oxygen level within fluid 600 utilizing, e.g., a fluorescence lifetime technique (FLT). Fluorescence sensor 601 includes housing 606, fluorescent material 602, diffuse reflector 604, excitation light source 612, and fluorescent light detector 614 (e.g., opposite fluorescent light source 612 in the x-direction and not visible in FIG. 6; see FIG. 7. Fluorescence sensor 601 may determine a parameter fluid 600 based on the sensed fluorescence. Once the determination of the parameter is made, a processor (e.g., processor 500 of FIG. 5) may control a user interface (e.g., user interface 504 on external device 24) to present an indication of the determined parameter. For example, processor 500 may control user interface 504 of external device 24 to present an indication of oxygen saturation of fluid 600 determined using fluorescence sensor 601.

Housing 606 may define and/or enclose a volume and may include a first aperture 608 and a second aperture 610 defined by one or more walls of housing 606. Each of first aperture 608 and second aperture 610 may be configured to allow fluid 600 to flow into and out of the volume defined by housing 606. While two apertures 608 and 610 are illustrated in FIG. 6, in some examples, housing 606 may include fewer or more apertures. Housing 606 may be substantially non-transmissive to light, e.g., excitation light, fluorescent light, and/or ambient light. For example, housing 606 may prevent substantially all light having various properties, such as particular wavelengths of excitation light from excitation light source 512 or fluorescent light from fluorescent material 614, from transmitting through walls of housing 606. Fluorescent material 602 may be disposed within the volume enclosed by housing 606. Fluorescent material 602 may be substantially similar to the fluorescent material described above with reference to sensor 20 of FIG. 1.

Housing 606 may support excitation light source 612 and fluorescent light detector 614. In the example shown, excitation light source 612 and fluorescent light detector 614 are illustrated as being opposite each other in the x-direction, however, excitation light source 612 and fluorescent light detector 614 may be positioned at any location on or within housing 606 that is suitable to illuminate diffuser 604 (by excitation light source 612) such that fluorescent material 602 receives a substantially uniform distribution of excitation light and such that fluorescent light detector 614 may measure an amount of fluoresced light substantially independent of view angle. In some examples, fluorescent light detector 614 may view fluorescent material 602 directly, and in other examples fluorescent light detector 614 may view diffuser 604 and receive fluoresced light that has been diffusely reflected from diffuse reflector 604.

Housing 606 may be configured to house, support or otherwise couple together one or more of excitation light source 612, fluorescent light detector 614, or diffuse reflector 604, and fluorescent material 602, e.g., in a desired arrangement. In some examples, housing 606 may be configured to be removably coupled to elongated body 12 and/or 62, e.g., to allow for a portion of fluorescence sensor 601 to be reusable with other catheters and/or catheter attachments. In some examples, housing 606 may be configured to fit and/or be disposed within lumen 34 and/or 54. In some examples, housing 606 may be an integrating sphere.

Excitation light source 612 may be configured to emit excitation light. Excitation light source 612 may be any suitable light device or devices configured to emit excitation light in the manner described herein. In some examples, excitation light source 612 includes an LED (light emitting diode), a laser, amplified natural lighting, HID (high-intensity discharge) and/or fluorescent and incandescent source capable of emitting excitation light, e.g., at an excitation wavelength. Excitation light source 612 emits a wavelength or range of wavelengths of light configured to excite (i.e. raise an energy state of) fluorescent material 602. The wavelength of excitation light may be different for differing fluorescent materials (e.g., different fluorescent material chemistries have different excitation frequencies). Excitation light source 612 may be powered by an onboard power source on fluorescence sensor 601 or maybe powered by external device 24 providing power through connection 38 (FIG. 2). In some examples, excitation light source 614 may emit a specific wavelength of light, that causes the fluorescent material to enter an excited state.

Fluorescent light detector 614 may be any type of light detector configured to detect fluorescent light, e.g., to detect the decay of fluorescent light from fluorescent material 602 over a period of time. In some examples, fluorescent light detector 614 may be a photodiode (e.g., PN photodiodes, PIN photodiodes, avalanche photodiodes (particularly well suited for fluorescence sensor due to their high sensitivity), and Schottky photodiodes), photoconductor (e.g., photoresistor), photovoltaic device (e.g., photocell), phototransistor, and/or photodiode. Fluorescent light detector 614 may detect fluoresced light between 300 nm and 800 nm. In some examples, processing circuitry 500 may process signals from fluorescent light detector 614 corresponding to the fluoresced light detected by fluorescent light detector 614 to detect the time fluorescent material 602 spends in the excited state or otherwise detect the rate of decay of the fluorescent light.

Diffuse reflector 604 may be disposed within the volume enclosed by housing 606. Diffuse reflector 604 may be substantially the same as the diffuse reflector described above with reference to sensor 20. In the example shown, diffuse reflector 604 is attached to or otherwise disposed on at least a portion of an inner surface of housing 606. In some examples, at least a portion of an inner surface of housing 606 may comprise diffuse reflector 604. Diffuse reflector 604 may be made of any suitable diffusely reflecting material at the excitation and fluorescence wavelengths, for example, flat white paint, barium sulfate (BaSO4), Spectralon®, polytetrafluoroethylene (PTFE), Teflon®, and the like.

Diffuse reflector 604 may be configured to diffuse and direct light from excitation light source 612 to fluorescent material 602. For example, diffuse reflector 604 may have various properties and/or structural features configured to preserve excitation light from excitation light source 612 within sensor 602 and spatially distribute the excitation light within sensor 602, such that fluorescent material 602 may receive excitation light that is relatively unaffected by flow variations of fluid 600 and/or ambient light from around sensor 606.

Diffuse reflector 604 may be configured to reflect excitation light incident on a surface of diffuse reflector 604. For example, diffuse reflector 604 may include one or more materials with a high reflectivity for excitation light emitted by excitation light source 612 and having a particular wavelength or range of wavelengths, such that the excitation light may be substantially contained within the volume of sensor 606. Diffuse reflector 604 may be configured to diffuse excitation light incident on a surface of diffuse reflector 604. For example, diffuse reflector 604 may include one or more materials or surface properties with diffuse scattering for excitation light emitted by excitation light source 612, such that the excitation light may be substantially dispersed within the volume of sensor 606. Diffuse reflector 604 may be configured to diffuse excitation light in a substantially uniform spatial distribution, e.g., such that the fluorescent material may receive a relatively uniform amount of excitation light. In some examples, diffuse reflector 604 may be a monolithic material configured to both diffuse and reflect incident excitation light, and in other examples diffuse reflector 604 may be a combination of both a diffuser configured to substantially diffuse and transmit incident excitation light and a reflector configured to reflect the excitation light.

Diffuse reflector 604 may be configured to diffuse and direct light from fluorescent material 602 to fluorescent light detector 614. For example, diffuse reflector 604 may have various properties and/or structural features configured to preserve fluorescent light from fluorescent material 602 within sensor 602 and spatially distribute the fluorescent light within sensor 602, such that fluorescent light detector 614 may receive fluorescent light that is relatively unaffected by flow variations of fluid 600 and/or ambient light from around sensor 606.

Diffuse reflector 604 may be configured to reflect fluorescent light incident on a surface of diffuse reflector 604. For example, diffuse reflector 604 may include one or more materials with a high reflectivity for fluorescent light emitted by fluorescent material 602 and having a particular wavelength or range of wavelengths, such that the fluorescent light may be substantially contained within the volume of sensor 606. Diffuse reflector 604 may be configured to diffuse fluorescent light incident on a surface of diffuse reflector 604. For example, diffuse reflector 604 may include one or more materials or surface properties with diffuse scattering for fluorescent light emitted by excitation light source 612, such that the fluorescent light may be substantially dispersed within the volume of sensor 606. Diffuse reflector 604 may be configured to diffuse fluoresced light in a substantially uniform spatial distribution, e.g., such that fluorescent light detector 614 may detect fluorescent light from fluorescent light material 602 independent of the view angle of fluorescent light detector 614 with respect to diffuse reflector 604. In some examples, diffuse reflector 604 may be a monolithic material configured to both diffuse and reflect incident fluorescent light, and in other examples diffuse reflector 604 may be a combination of both a diffuser configured to substantially diffuse and transmit incident fluorescent light and a reflector configured to reflect the fluorescent light.

In one example, fluorescence sensor 601 is configured to sense oxygen in fluid 600 (e.g., oxygen concentration) using a FLT and based on a fluorescence response from a fluorescent material, such as fluorescent material 602. In this technique, fluorescent material 602 is exposed to excitation light (which may be a specific wavelength or range of wavelengths) emitted from excitation light source 612, such as directly from excitation light source 612 or reflected off one or more surfaces of diffuse reflector 604. Fluorescent material 602 (referred to as a fluorescence lifetime material or an optrode), glows and/or fluoresces when exposed to the excitation light, which is detected by fluorescent light detector 614, such as directly from fluorescent material 602 or reflected off one or more surfaces of diffuse reflector 604. In specific materials used for fluorescent material 602, the rate at which the glow fades is inversely proportional to the amount of oxygen the fluorescent material exposed to. In these fluorescent materials, the more oxygen (i.e., higher concentration of oxygen) that is present the faster the glow fades. By measuring the rate of glow and/or fluorescence response decay in calibrated optrode with fluorescent light detector 614, fluorescence sensor 601 may measure the amount of oxygen in fluid 600, e.g., accurately and/or substantially continuously.

As described herein, fluorescence sensor 601 may be an optical sensor device that optically measures a specific substance (e.g., oxygen in fluid 600) with the aid of a fluorescent material 602 (which may be referred to as an optode or optrode). For FLT, e.g., fluorescence sensor 601 may utilize luminescence (e.g., fluorescence and phosphorescence) or chemiluminescence to measure the oxygen within fluid 600 within lumen 34 and/or lumen 54. However, other methods of optical measurement may be used. In some examples, optical sensing techniques such as reflection, absorption, evanescent wave, surface plasmon resonance, may be used.

Fluorescent material 602 may be any suitable material configured to fluoresce in response to being exposed to excitation light from excitation light source 612 in the manner described herein. When exposed to excitation light, fluorescent material 602 releases fluorescent light. The fluorescent light may be quenched, or caused to dissipate, by specific analytes (e.g., oxygen) in fluid 600. The fluorescent light to oxygen ratio within fluid 600 may not be linear. For example, fluorescence sensor 601 may have a greater sensitivity at low oxygen concentration, (e.g., when the fluorescent light is the greatest) then at high oxygen concentration (e.g., when the fluorescent light is the lowest). Fluorescence sensor 601 may operate in a region of 0-100% oxygen saturation in fluids containing mostly water, such as urine, with a calibration for the type of material reacting with fluorescent material 602.

In some examples, sensor 601 may also include filters to optimize the delivery of excitation light or sensing of fluoresced light. With filters, excitation light source 612 and fluorescent light detector 614 may be less precise and thus less expensive alternatives for excitation light source 612 and fluorescent light detector 614 may be used.

As described above, fluorescence sensor 601 may be configured to measure one or more parameters of fluid 600 by measuring a fluorescence lifetime (FLT) of a fluorescence response from fluorescent material 602. FLT may be the time fluorescent material 602 spends in the excited state ($T_{es}$). In some examples, the FLT may vary from picoseconds to hundreds of nanoseconds depending on the fluorescent material. FLT may not be substantially affected by fluorescence concentration, absorption by fluid 600, thickness of fluid 600, method of measurement, fluorescence intensity, photo-bleaching and/or excitation intensity. However, FLT may be affected by external factors, such as temperature (discussed below, which may be calibrated for), polarity, and the presence of fluorescence quenchers (e.g., oxygen).

For fluorescence sensor 601 to measure a fluid parameter based on FLT, fluorescent material 602 may be in fluid communication with fluid 600. Excitation light source 612, when powered on by processing circuitry 500 or a separate power source onboard (not shown), may emit excitation light, e.g., at a specific wavelength to expose fluorescent material 602 to the emitted excitation light.

Fluorescent material 602 within fluid 600, as discussed above, may be configured to fluoresce when exposed to excitation light. Excitation light detector 614 may detect the fluoresced light and processing circuitry 520 may then determine the amount of oxygen within fluid 600 by recording the time for fluorescent light ($T_f$) to quench (or dissipate) or otherwise decay. Processing circuitry 500 may then determine the time to dissipate ($T_f$) with ($T_{es}$) and based upon this difference, determine how much oxygen is present within fluid 600. Further, processing circuitry such as processing circuitry 500 may calibrate for the temperature of fluid 600, which may have an effect on how quickly the fluorescent light dissipates.

In another example, fluorescent material 602 may be excited with excitation light pulses (e.g., light initiated in a sine wave pulse). Processing circuitry 500 may then determine a frequency shift of the fluorescent material response that measures the fluorescence decay time continuously. In another example, when fluorescent material 602 are excited, the fluorescence saturation time may be measured and determined by processing circuitry 500, where the saturation time is proportional to oxygen content.

Processing circuitry 500 may use time for fluorescent light 616 ($T_f$) to determine an amount of oxygen within fluid 600 within lumen 34 and/or 54. As discussed, the fluorescent light has a fluorescence excitation time limit ($T_{es}$) that represents a maximum time at which fluorescent material 602 may fluoresce. Various factors, such as an amount or concentration of oxygen in fluid 600, may shorten this excitation time. For example, when oxygen molecules are present in fluid 600 and collide with fluorescent material 602, the oxygen molecules may quench the fluorescent light, such as by forming ground complexes with the fluorescence material 602 or absorbing energy from fluorescent material 602 that may otherwise be emitted as fluorescent light. If fluid 600 has no oxygen present, then fluorescence time ($T_f$) may be close to or equal to the excitation state time ($T_{es}$). On the other hand, if fluid 600 has a 100% oxygen saturation, then fluorescence time ($T_f$) should be zero or substantially zero. As stated above, the relationship between fluorescence time ($T_f$) and oxygen concentration may be non-linear.

Processing circuitry 500 may determine an amount and/or concentration of oxygen based on the determined fluorescence time of fluorescent material 602 detected by fluorescent light detector 614. In some examples, processing circuitry 500 may use an algorithm to determine the amount of oxygen within fluid 600. In another example, processing circuitry 500 may utilize a lookup table stored on memory 502 and/or memory 19, where an oxygen content of fluid 600 is dependent on fluorescence time ($T_f$) and the temperature of fluid 600 (e.g., discussed above, temperature also affect fluorescence time).

As discussed above, the accuracy of fluorescence sensor 601 may be temperature dependent as temperature affects the fluorescence time ($T_f$). Thus, to provide accurate sensor readings, fluorescence sensor 601 may be calibrated, e.g., in real time, to obtain an accurate oxygen measurement. To obtain this measurement the temperature of fluid 600 may be used. Therefore, the more accurately the temperature of fluid 600 is known, the more accurate a reading of oxygen can be obtained from fluorescence sensor 601. Processing circuitry 500 may use the temperature data collected from temperature sensors, an estimated temperature based on a patient's body temperature, another sensor coupled to external device 24 or a temperature inputted by a user at user interface 504. Processing circuitry 500 may use the temperature to input into, e.g., an algorithm or a look up table to calibrate the oxygen calculation based on temperature of fluid 600 in combination with the rate of fluorescence decay detected by fluorescent light detector 614.

Figure 7:
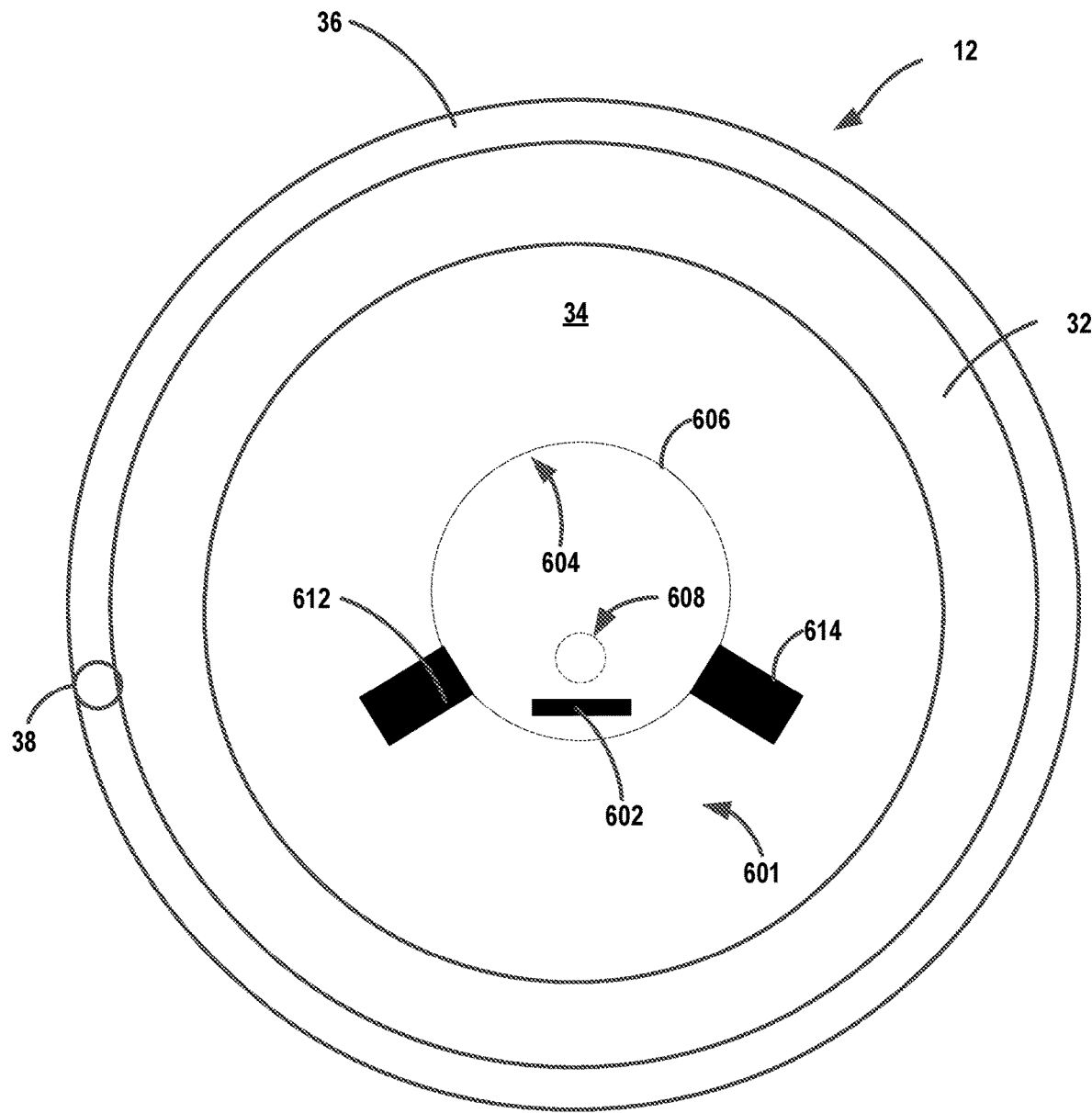
FIG. 7 is a diagram illustrating another view of the example sensor of FIG. 6 used with a medical device according to the techniques of this disclosure.

FIG. 7 is a diagram illustrating an example cross-section of medical device 10 where the cross-section is taken along line 1-1 in FIG. 1 in a direction perpendicular to central longitudinal axis 16, and/or a medical device 50 where the cross-section is taken along line 2-2 in FIG. 3, and illustrating an example fluorescence sensor 601 used with medical device 10 and/or medical device 50, according to the techniques of this disclosure. FIG. 7 illustrates fluorescence sensor 601 within lumen 34 or lumen 54 from the perpendicular direction, similar to the view of medical device 10 and/or medical device 50 illustrated in FIG. 2 and shows one arrangement of excitation light source 612 and fluorescent light detector 614.

Figure 8:
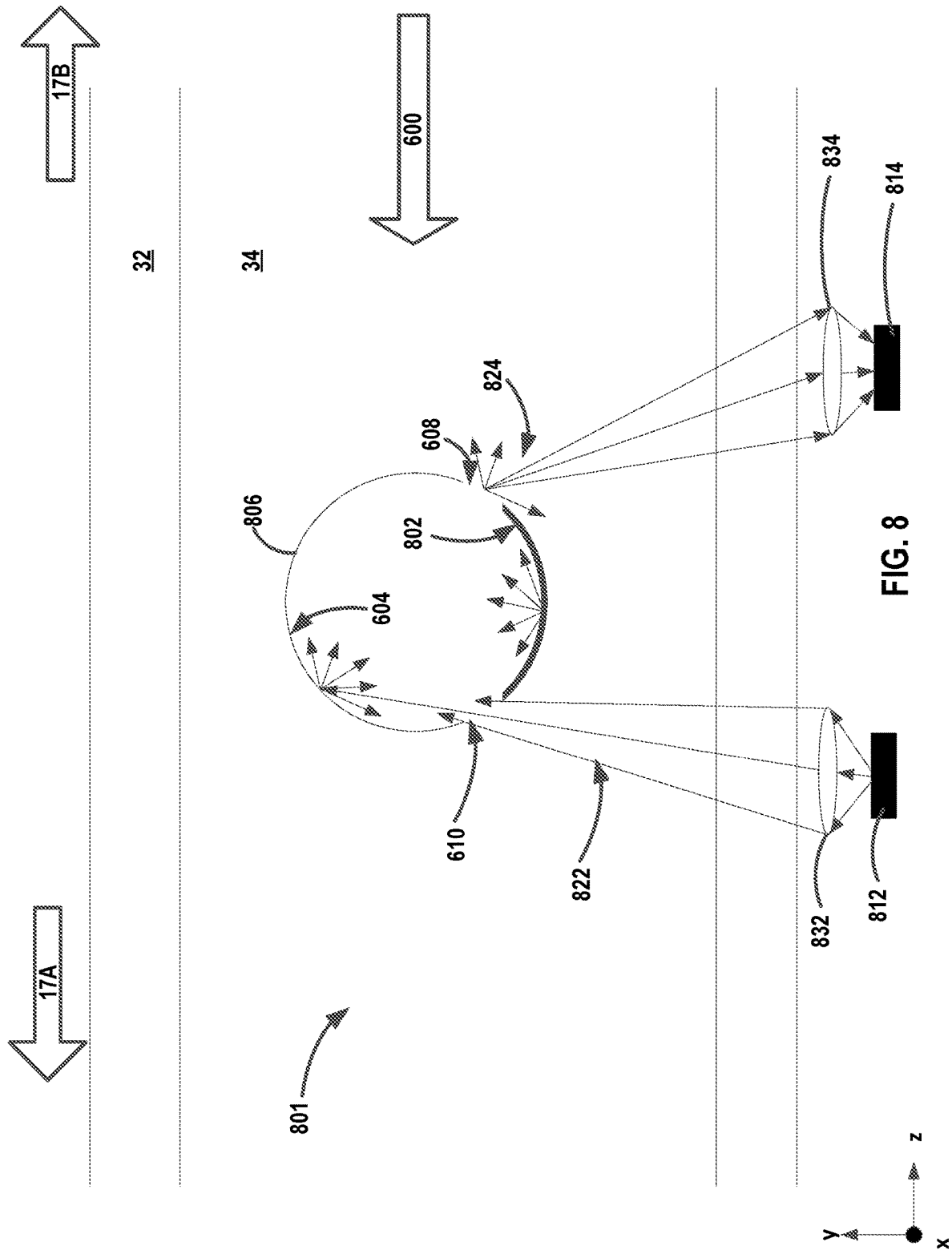
FIG. 8 is a diagram illustrating another example sensor used with a medical device according to the techniques of this disclosure.

FIG. 8 is a diagram illustrating an example fluorescence sensor 801 used with a medical device 10 and/or a medical device 50, according to the techniques of this disclosure. Fluorescence sensor 801 may be an example of sensor 20 of medical device 10 (FIG. 1) and/or medical device 50 (FIG. 3), and fluorescence sensor 801 may be used in place of sensor 20, used in combination with sensor 20 and other sensors such as temperature sensors, or in addition to sensor 20 and other sensors such as temperature sensors. Fluorescence sensor 801 may be substantially similar to fluorescence sensor 601 described above but having a different arrangement of excitation light source 812, fluorescent light detector 814, and placement/arrangement of fluorescent material within a housing. In the example shown, fluid 600 is flowing from proximal portion 17B to distal portion 17A of medical device 10, as indicated by the directional arrow. Additionally or alternatively, fluid 600 may flow from proximal end 62B to distal end 62A of medical device 50.

Fluorescence sensor 801 may be configured to determine an oxygen level within fluid 600 utilizing, e.g., FLT substantially similar to fluorescence sensor 601. Fluorescence sensor 801 includes housing 806, excitation light source 812, and fluorescent light detector 814. Fluorescence sensor 801 may determine a parameter based on the sensed fluorescence. Once the determination is made, a processor (e.g., processor 500 of FIG. 5) may control a user interface (e.g., user interface 504 on external device 24) to present an indication of the determined value. For example, processor 500 may control user interface 504 of external device 24 to present an indication of oxygen saturation of fluid 600 determined with fluorescence sensor 801, substantially similar to fluorescence sensor 601 described above.

Housing 806 may define and/or enclose a volume and may include a first aperture 608 and a second aperture 610 defined by one or more housing 606 walls and configured to allow fluid 600 to flow into and out of the volume defined by housing 806 and to allow excitation light 822 and fluorescent light 824 to enter and exit the volume defined by housing 806. In some examples, housing 806 may include fewer or more apertures. In some examples, housing 806 may be configured to be removably coupled to elongated body 12 and/or 62, e.g., to allow for a portion of fluorescence sensor 801 to be reusable with other catheters and/or catheter attachments. In some examples, housing 806 may be an integrating sphere.

Sensor 801 may further include diffuse reflector 604 disposed within the volume enclosed by housing 806. In the example shown, diffuse reflector 604 is attached to or otherwise disposed on, or forms, at least a portion of an inner surface of housing 806. In some examples, at least a portion of an inner surface of housing 806 may comprise diffuse reflector 604. Diffuse reflector 604 illustrated in FIG. 8 may be substantially similar to any previous diffuse reflector described above.

Sensor 801 may further include a fluorescent material 802 disposed within the volume enclosed by housing 606. Fluorescent material 802 may be substantially similar to the fluorescent material described above with reference to sensor 20 and fluorescent sensor 601. In the example shown, fluorescent material 802 may be disposed on, or may form, at least a portion of an inner surface of housing 806. In the example shown, fluorescent material 802 is configured such that it does not directly receive excitation light 822. For example, housing 806, diffuse reflector 804, fluorescent material 802, first aperture 608 and/or second aperture 610, and excitation light source 812 may be arranged such that excitation light 822 is incident on and reflects from diffuse reflector 604 at least once before being received or is incident on fluorescent material 802. In some examples, such an arrangement may reduce and/or eliminate variation in the amount of excitation light 822 incident on fluorescent material 802 due to changes in alignment between excitation light source 812 and fluorescent material 802.

Excitation light source 812 may be configured to emit excitation light 822 and may be substantially similar to excitation light source 612 described above. In some examples, excitation light source 812 may be located outside of housing 806, e.g., excitation light source 812 may be located anywhere suitable for emitting light through aperture 610 and/or aperture 608 and incident on diffuse reflector 604. In the example shown, excitation light source 812 may be located outside of elongated body 12 and/or elongated body 62 and as close to elongated body 12 and/or elongated body 62 as possible.

Fluorescent light detector 814 may be configured to detect fluorescent light 824 and may be substantially similar to fluorescent light detector 814 described above. In some examples, fluorescent light detector 814 may be located outside of housing 806, e.g., fluorescent light detector 814 may be located anywhere suitable for receiving fluorescent light 824 from housing 806, e.g., via aperture 608 and/or aperture 610. In the example shown, fluorescent light detector 814 may be located outside of elongated body 12 and/or elongated body 62 and as close to elongated body 12 and/or elongated body 62 as possible.

Excitation light source 812 may emit excitation light 822 through elongated body 12 and/or 62. In some examples, lumen wall 32 and/or 52 may be transparent to excitation light 822 and fluorescent light 824 or otherwise configured to allow excitation light 822 and fluorescent light 824 to be transmitted through lumen wall 32 and/or 52.

In some examples, excitation light source 812 may include one or more lenses 832 and fluorescent light detector 814 may include one or more lenses 834. The one or more lenses 832 may be configured to focus and/or increase the amount of excitation light 822 to diffuse reflector 604 through aperture 610 and/or aperture 608. The one or more lenses 834 may be configured to focus and/or increase the amount of fluorescent light 824 on fluorescent light detector 814. Lens 832 may focus and/or increase the amount of excitation light 822 from excitation light source 812 increase its intensity of excitation light received by diffuse reflector 604, and subsequently fluorescent material 802, and reduce the performance requirement of excitation light source 812. Lens 834 may focus and/or increase the amount of fluorescent light 824 on fluorescent light detector 814 to increase its intensity and reduce the performance requirement of fluorescent light detector 814. In some examples, lenses 832 and 834 may be optical glass, crystals, plastics, mirrors or other material that focuses light in the manner described herein. Lenses 832 and 834 may be configured to be disposable or re-usable as part of fluorescence sensor 801. In some examples, sensor 801 may also include filters to optimize the delivery of excitation light 822 or sensing of fluorescent light 824. With filters, excitation light source 812 and fluorescent light detector 814 may be less precise and thus less expensive alternatives for excitation light source 812 and fluorescent light detector 814 may be used.

In some examples, excitation light source 812 and fluorescent light detector 814 may be expensive relative to other components of fluorescent sensor 801 and/or medical device 10 and/or medical device 50. Excitation light source 812 and fluorescent light detector 814 may be reusable and detachably coupled to elongated body 12 and/or 62, e.g., either separate from each other or together. In other examples, each of excitation light source 812 and fluorescent light detector 814 may be part of or integral with elongated body 12 and/or 62 or may be separate and coupled to elongated body 12 and/or 62 for use during a procedure. In some examples, lens 832 and/or lens 834 may be added, e.g., for improved performance of excitation light source 812 and fluorescent light detector 814 and may be placed on elongated body 12 and/or 62 in between housing 806 and excitation light source 812 and fluorescent light detector 814. In some examples, lens 832 and/or lens 834 may be disposed of along with elongated body 12 and/or 62 and fluorescent probes 602 when the patient no longer needs medical device 10 and/or a catheter.

Figure 9:
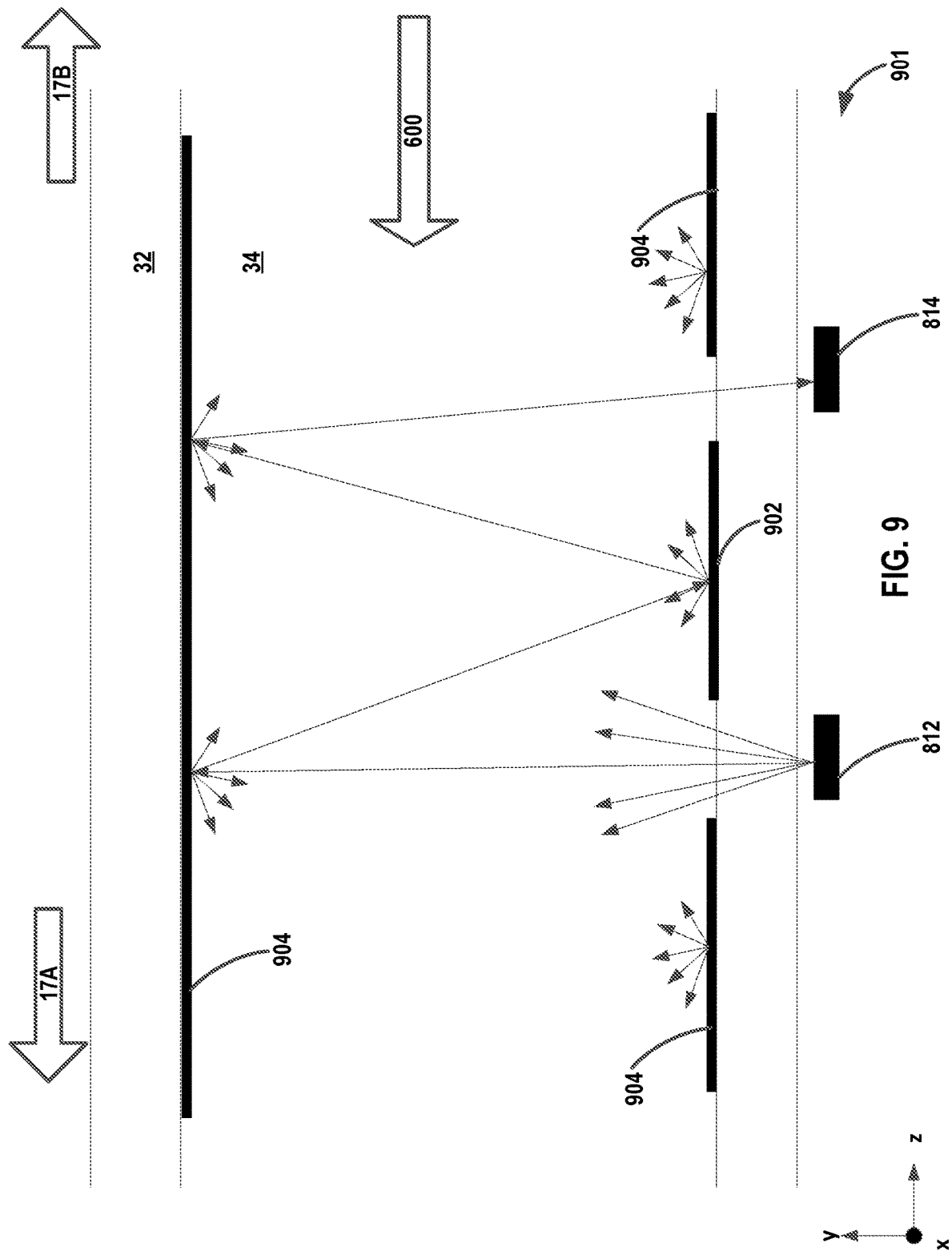
FIG. 9 is a flow diagram illustrating another example technique for monitoring or otherwise sensing oxygen and a flow rate of a fluid within a lumen using the sensor of FIG. 8 according to the techniques of this disclosure.

FIG. 9 is a diagram illustrating an example fluorescence sensor 901 used with a medical device 10 and/or a medical device 50, according to the techniques of this disclosure. Fluorescence sensor 901 may be an example of sensor 20 of medical device 10 (FIG. 1) and/or medical device 50 (FIG. 3), and fluorescence sensor 901 may be used in place of sensor 20, used in combination with sensor 20 and other sensors such as temperature sensors, or in addition to sensor 20 and other sensors such as temperature sensors. Fluorescence sensor 901 may be substantially similar to fluorescence sensor 801 described above but having a different arrangement of excitation light source 812, fluorescent light detector 814, and placement/arrangement of both diffuse reflector 904 and fluorescent material 902, e.g., without a housing analogous to housing 606 and/or housing 806. For example, fluorescence sensor 901 may use elongated body 12 and/or 62 as the housing for an effective "integrating sphere" where at least a portion of the inner surface of lumen 34 and/or 54 include a diffuse reflector and fluorescent material. In the example shown, fluid 600 is flowing from proximal portion 17B to distal portion 17A of medical device 10, as indicated by the directional arrow. Additionally or alternatively, fluid 600 may flow from proximal end 62B to distal end 62A of medical device 50.

Fluorescence sensor 901 may be configured to determine an oxygen level within fluid 600 utilizing, e.g., FLT substantially similar to any of fluorescence sensors 20, 601, and 801 described above. Fluorescence sensor 901 includes excitation light source 812, and fluorescent light detector 814. Fluorescence sensor 901 may determine a parameter based on the sensed fluorescence. Once the determination is made, a processor (e.g., processor 500 of FIG. 5) may control a user interface (e.g., user interface 504 on external device 24) to present an indication of the determined value. For example, processor 500 may control user interface 504 of external device 24 to present an indication of oxygen saturation of fluid 600 determined with fluorescence sensor 801, substantially similar to fluorescence sensors 601 and 801 described above.

Sensor 901 may include diffuse reflector 904 disposed within lumen 34 and/or lumen 54. In some examples, diffuse reflector 904 may be disposed within lumen wall 32 and/or 52, and in other examples diffuse reflector 904 may be disposed on an outside surface of elongated body 12 and/or 62, e.g., on an outside surface of lumen wall 32 and/or 52. Diffuse reflector 904 illustrated in FIG. 9 may be substantially similar to any previous diffuse reflector described above.

Sensor 901 may include a fluorescent material 902 disposed within lumen 34 and/or lumen 54. Fluorescent material 902 may be substantially similar to the fluorescent material described above with reference to sensor 20 and fluorescent sensors 601 and 801. In the example shown, fluorescent material 902 may be disposed on, or may form, at least a portion of an inner surface of lumen wall 32 and/or 52.

In the example shown, fluorescent material 902 is configured such that it does not directly receive excitation light. For example, one or more apertures within and/or between diffuse reflector 904 and fluorescent material 902 may allow excitation light from excitation light source 812 to transmit into lumen 32 and/or 52 and to be incident on reflect from diffuse reflector 904 at least once before being received or incident on fluorescent material 902. In some examples, such an arrangement may reduce and/or eliminate variation in the amount of excitation light incident on fluorescent material due to changes in alignment between excitation light source 812 and fluorescent material 902.

Excitation light source 812 may be configured to emit excitation light and may be substantially similar to excitation light source 812 described above. In some examples, excitation light source 812 may be located anywhere suitable for emitting excitation light to diffuse reflector 904. In the example shown, excitation light source 812 may be located outside of elongated body 12 and/or elongated body 62 and as close to elongated body 12 and/or elongated body 62 as possible. Excitation light source 812 may emit excitation light through elongated body 12 and/or 62. In some examples, lumen wall 32 and/or 52 may be transparent to excitation light and fluorescent light or otherwise configured to allow excitation light and fluorescent light 824 to be transmitted through lumen wall 32 and/or 52.

Fluorescent light detector 814 may be configured to detect fluorescent light and may be substantially similar to fluorescent light detector 814 described above. In some examples, fluorescent light detector 814 may be located anywhere suitable for receiving fluorescent light from fluorescent material 902, e.g., either directly (not shown) and/or after reflection of fluorescent light from diffuse reflector 904. In the example shown, fluorescent light detector 814 may be located outside of elongated body 12 and/or elongated body 62 and as close to elongated body 12 and/or elongated body 62 as possible.

In some examples, excitation light source 812 and fluorescent detector 814 may include one or more lenses and filters, e.g., such as lenses 832 and 834 and filters described above, and may be reusable and detachably coupled to elongated body 12 and/or 62, separate from each other or together, or may be a part of or integral with elongated body 12 and/or 62.

Figure 10:
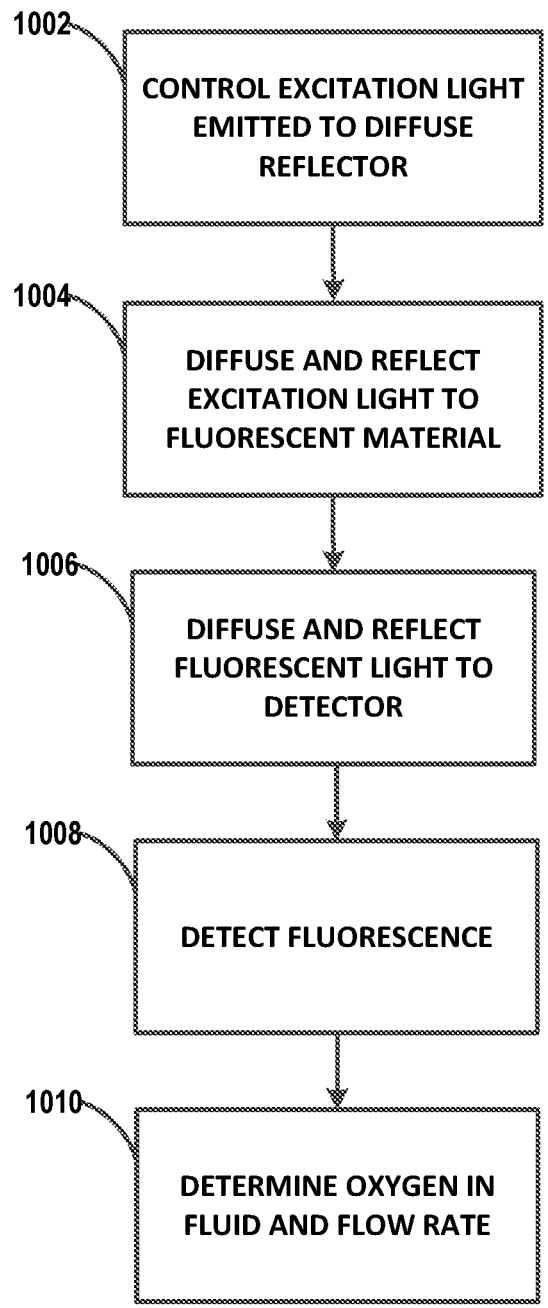
FIG. 10 is a flow diagram illustrating an example technique for monitoring or otherwise sensing oxygen within a fluid, according to the techniques of this disclosure.

FIG. 10 is a flow diagram illustrating an example technique for monitoring or otherwise sensing an amount and/or concentration of oxygen in a fluid, according to techniques of this disclosure. FIG. 10 will be described with respect to any of FIGS. 6-9.

Processing circuitry 500 may control excitation light source 612 and/or 812 to emit excitation light to be incident on diffuse reflector 604, 804, or 904 (1002). In some examples, fluorescence sensors 601, 801, and 901 may be a stand-alone sensor having its own processing circuitry to control light source 612 and/or 812 and to control light detector 614 and/or 814. In some examples, processing circuitry 500 may control light source 612 and/or 812 to emit excitation light in a particular range of wavelengths corresponding to an excitation spectrum of the fluorescence material 602, 802, or 902.

Diffuse reflector 604, 804, or 904 may diffuse and reflect excitation light towards fluorescent material 602, 802, or 902 (1004). Diffusing and reflecting excitation light before exposing fluorescent material 602, 802, or 902 to the excitation light may reduce and/or eliminate variation in the amount of excitation light incident on fluorescent material 802 due to changes in alignment between excitation light source 612 and/or 812 and fluorescent material 602, 802, or 902.

Diffuse reflector 604, 804, or 904 may diffuse and reflect fluorescent light towards fluorescent light detector 614 and/or 814 (1006). Diffusing and reflecting fluorescent light emitted by fluorescent material 602, 802, or 902 to the excitation light may reduce and/or eliminate variation in the amount of fluorescent light incident on fluorescent light detector 614 and/or 814 due to changes in alignment between fluorescent light detector 614 and/or 814 and fluorescent material 602, 802, or 902.

Fluorescent light detector 614 and/or 814 may detect fluorescent light from fluorescent material 602, 802, or 902 diffused and reflected via diffuse reflector 604, 804, or 904 (1008). In some examples, the fluorescent light is indicative of a composition of fluid 600, for example, an amount of oxygen of fluid 600.

Processing circuitry 500 may determine an amount oxygen in fluid 600 within lumen 34 and/or 54 based on the detected fluorescence, e.g., based on FLT ($T_f$) 1010). The greater the amount of oxygen present the lower the amount of fluorescent light detected and the lower the amount of oxygen the higher the amount of fluorescent light detected. For example, in some instances, processing circuitry 500 may determine a concentration of oxygen in fluid 600. Processing circuitry 500 may continually monitor fluorescent light detector 614 and/or 814 sensing the FLT ($T_f$). Based upon $T_f$ processing circuitry may utilize a lookup table or an algorithm to determine an oxygen level within lumen 34 and/or 54. Further, processing circuitry 500 may determine an oxygen level at a specific point in time, or a running average of oxygen amount or even determine a trend of oxygen with lumen 34 and/or 54 over time.

In some examples, medical device 10 and/or 50, or sensor 20, fluorescent sensor 601, 801, or 901 may include a temperature sensor configured to measure the temperature of fluid 600. Processing circuitry 500 may determine a temperature of fluid 600 within lumen 34 and/or 54 based on the temperature measured by a temperature sensor and as part of the determination of the oxygen in fluid 600. Fluorescence material may be temperature-dependent and to obtain a more accurate oxygen measurement the temperature of fluid 600 may be useful in calibrating the oxygen measurement. Processing circuitry 500 may use the temperature data collected from any of a number of data sources, for example, temperature sensors, an estimated temperature based on a patient's body temperature, another sensor coupled to external device 24 or a temperature inputted by a user at user interface 504. Processing circuitry 500 may use the temperature data to input into, e.g., an algorithm or a look up table to calibrate the oxygen calculation based on temperature of fluid 600 in combination with the rate of fluorescence decay detected by fluorescent light detector 614 and/or 814.

Any suitable technique may be employed by processing circuitry 500 to determine the level of oxygen and flow rate of fluid 600 based on fluorescent light detected by fluorescent light detector 614 and/or 814.

In some examples, processing circuitry 500 may reference a look up table in memory 502 to determine the oxygen level within fluid 600 based upon the detected fluorescence (e.g., alone or in combination with the determined temperature and determined flow rate). In some examples, processing circuitry 500 may execute an algorithm on memory 502 which calculates the oxygen level based upon fluorescent light detected and, in some examples, the determined temperature of fluid 600. In some examples, processing circuitry 500 may reference a lookup table stored in memory 502 or memory 19. The lookup table may have a correlation for a specific fluorescence material and what the fluorescence material's fluorescence time ($T_f$) is based upon a determined temperature of fluid 600. Based upon the temperature of fluid 600, the flow rate, and the fluorescence time ($T_f$) sensed by fluorescent light detector 614 and/or 814 a lookup table may provide a corresponding oxygen level of fluid 600 based on the known variables. In another example, a lookup table may be implemented in algorithmic form where the variables are inputted into the algorithm by processing circuitry 500 and an oxygen level is presented in display form on user interface 504 and/or through an audible form by a speaker on external device 24. In some examples, an alarm may be implemented through user interface 504 visually and/or audibly through a speaker if the oxygen level deviated outside of an upper or lower threshold. In another example, processing circuitry 500 may execute software 508 to perform the oxygen level determination based upon fluorescence time ($T_f$) and/or temperature and flow rate.

Various examples have been described. These and other examples are within the scope of the following claims. For purposes of this disclosure, the operations shown in the figures do not need to be executed in the manner suggested by the illustrations and, unless specifically stated so, may be executed in any order. Further, the term substantially is to be given its standard definition of to a great or significant extent or for the most part; essentially. The following is a non-limiting list of examples that are in accordance with one or more techniques of this disclosure.

Example 1: A system includes an elongated body defining a lumen, the elongated body comprising a proximal portion and a distal portion; a fluorescent material configured to be in fluid communication with a fluid in the lumen; and a diffuse reflector configured to: diffuse excitation light received from an excitation light source and direct the diffused excitation light toward the fluorescent material; and diffuse the fluoresced light received from the fluorescence material and direct the fluoresced light toward a fluorescent light detector.

Example 2: The system of example 1, wherein the fluorescent material is configured to fluoresce in response to the excitation light from the excitation light source incident on the fluorescence material via the diffuse reflector, wherein the amount of fluoresced light measured by the fluorescent light detector is substantially independent of an angle of incidence of the excitation light from the excitation light source on the diffuse reflector, and wherein the amount of fluoresced light measured by the fluorescent light detector is substantially independent of a view angle of the fluorescent light detector with respect to the diffuse reflector.

Example 3: The system of example 1 or 2, further includes a housing comprising at least one aperture and configured to allow the liquid to enter and exit the housing, wherein the fluorescence material is disposed within the housing, wherein the diffuse reflector is disposed within the housing, and wherein the housing is configured to substantially block the fluorescence material and the diffuse reflector from ambient light.

Example 4: The system of example 3, wherein the housing is configured to fit within the lumen.

Example 5: The system of example 3 or 4, wherein the excitation light source is configured to direct excitation light through the at least one aperture and to the diffuse reflector, and wherein the fluorescent light detector is configured to receive fluoresced light from the diffuse reflector through the at least one aperture.

Example 6: The system of any of examples 3 to 5, wherein the diffuse reflector forms at least a portion of an inner surface of the housing.

Example 7: The system of any of examples 3 to 6, wherein the fluorescence material forms at least a portion of the inner surface of the housing.

Example 8: The system of any of examples 1 to 7, further includes the excitation light source configured to emit the excitation light; and the fluorescent light detector configured to measure an amount of the fluoresced light.

Example 9: The system of example 8, wherein the excitation light source and the fluorescent light detector are each releasably coupled to the elongated body.

Example 10: The system of example 8 or 9, further comprising a computing device configured to determine at least one of an amount of oxygen or a concentration of oxygen in the fluid based on the amount of fluoresced light detected by the fluorescent light detector.

Example 11: The system of any of examples 1 to 10, wherein the elongated body comprises a catheter.

Example 12: A method includes controlling an excitation light source to emit excitation light toward a first diffuse reflector, wherein the first diffuse reflector is configured to diffuse the emitted excitation light to expose a fluorescent material to the emitted excitation light, wherein the fluorescent material is disposed within a lumen defined by an elongated body comprising a proximal portion and a distal portion, and wherein the fluorescent material is configured to fluoresce light toward a second diffuse reflector when exposed to the emitted excitation light; detecting, with a fluorescent light detector, an amount of fluoresced light from the second diffuse reflector, wherein the second diffuse reflector is configured to diffuse the fluoresced light to expose the fluorescent light detector to the fluoresced light; and determining, based on the amount of the detected fluoresced light, at least one of an amount of oxygen or a concentration of oxygen in the fluid within the lumen.

Example 13: The method of example 12, wherein the first and second diffuse reflector are the same diffuse reflector.

Example 14: The method of example 12 or 13, wherein the amount of fluoresced light detected by the fluorescent light detector is substantially independent of the angle of incidence of the excitation light from the excitation light source on the diffuse reflector, wherein the amount of fluoresced light measured by the fluorescent light detector is substantially independent of the view angle of the fluorescent light detector with respect to the diffuse reflector.

Example 15: The method of any of examples 12 to 14, wherein the fluorescence material and the diffuse reflector are disposed within a housing configured to block the fluorescent material from ambient light, and wherein the housing comprises at least one aperture configured to allow the fluid to enter and exit the housing.

Example 16: The method of example 15, further comprising positioning the housing within the lumen.

Example 17: A system includes an elongated body defining a lumen, the elongated body comprising a proximal portion and a distal portion; an integrating sphere disposed within the lumen, the integrating sphere includes a housing comprising at least one aperture, wherein the housing is configured to allow the liquid to enter and exit the housing, a fluorescent material disposed on at least a portion of an inner surface of the housing, wherein the fluorescent material is configured to be in fluid communication with a fluid within the lumen; and a diffuse reflector forming at least a portion of an inner surface of the housing, wherein the diffuse reflector is configured to: diffuse excitation light received from an excitation light source within the lumen; direct the diffused excitation light towards the fluorescent material; and diffuse the fluoresced light received from the fluorescent material within the integrating sphere.

Example 18: The system of example 17, wherein the fluorescent material is configured to fluoresce in response to the excitation light from the excitation light source incident on the fluorescence material via the diffuse reflector, wherein the amount of fluoresced light measured by the fluorescent light detector is substantially independent of an angle of incidence of the excitation light from the excitation light source on the diffuse reflector, and wherein the amount of fluoresced light measured by the fluorescent light detector is substantially independent of a view angle of the fluorescent light detector with respect to the diffuse reflector.

Example 19: The system of example 17 or 18, further includes the excitation light source coupled to the integrating sphere and configured to emit the excitation light; and the fluorescent light detector coupled to the integrating sphere and configured to measure an amount of the fluoresced light.

Example 20: The system of example 19, further comprising a computing device configured to determine at least one of an amount of oxygen or a concentration of oxygen in the fluid based on the amount of fluoresced light detected by the fluorescent light detector.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some respects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components. Also, the techniques may be fully implemented in one or more circuits or logic elements.

What is claimed is:

1. A method comprising:
   controlling an excitation light source to emit excitation light toward a first diffuse reflector, wherein the first diffuse reflector is configured to diffuse the emitted excitation light to expose a fluorescent material to the emitted excitation light, wherein the fluorescent material is disposed within a lumen defined by an elongated body comprising a proximal portion and a distal portion, and wherein the fluorescent material is configured to fluoresce light toward a second diffuse reflector when exposed to the emitted excitation light;
   detecting, with a fluorescent light detector, an amount of fluoresced light from the second diffuse reflector, wherein the second diffuse reflector is configured to diffuse the fluoresced light to expose the fluorescent light detector to the fluoresced light; and
   determining, based on the amount of the detected fluoresced light, at least one of an amount of oxygen or a concentration of oxygen in the fluid within the lumen.

2. The method of claim 1, wherein the first and second diffuse reflector are the same diffuse reflector.

3. The method of claim 1,
   wherein the amount of fluoresced light detected by the fluorescent light detector is substantially independent of the angle of incidence of the excitation light from the excitation light source on the diffuse reflector,
   wherein the amount of fluoresced light measured by the fluorescent light detector is substantially independent of the view angle of the fluorescent light detector with respect to the diffuse reflector.

4. The method of claim 1,
   wherein the fluorescence material and the diffuse reflector are disposed within a housing configured to block the fluorescent material from ambient light, and
   wherein the housing comprises at least one aperture configured to allow the fluid to enter and exit the housing.

5. The method of claim 4, further comprising positioning the housing within the lumen.

6. A system comprising:
   an elongated body defining a lumen, the elongated body comprising a proximal portion and a distal portion;
   an integrating sphere disposed within the lumen, the integrating sphere comprising:
      a housing comprising at least one aperture, wherein the housing is configured to allow the liquid to enter and exit the housing,
      a fluorescent material disposed on at least a portion of an inner surface of the housing, wherein the fluorescent material is configured to be in fluid communication with a fluid within the lumen; and
      a diffuse reflector forming at least a portion of an inner surface of the housing, wherein the diffuse reflector is configured to:
         diffuse excitation light received from an excitation light source within the lumen;
         direct the diffused excitation light towards the fluorescent material; and
         diffuse the fluoresced light received from the fluorescent material within the integrating sphere.

7. The system of claim 6,
   wherein the fluorescent material is configured to fluoresce in response to the excitation light from the excitation light source incident on the fluorescence material via the diffuse reflector,
   wherein the amount of fluoresced light measured by the fluorescent light detector is substantially independent of an angle of incidence of the excitation light from the excitation light source on the diffuse reflector, and
   wherein the amount of fluoresced light measured by the fluorescent light detector is substantially independent of a view angle of the fluorescent light detector with respect to the diffuse reflector.

8. The system of claim 6, further comprising:
   the excitation light source coupled to the integrating sphere and configured to emit the excitation light; and
   the fluorescent light detector coupled to the integrating sphere and configured to measure an amount of the fluoresced light.

9. The system of claim 8, further comprising a computing device configured to determine at least one of an amount of oxygen or a concentration of oxygen in the fluid based on the amount of fluoresced light detected by the fluorescent light detector.

* * * * *